US007306620B2

(12) United States Patent
Cumbie

(10) Patent No.: US 7,306,620 B2
(45) Date of Patent: Dec. 11, 2007

(54) PREVENTION AND TREATMENT OF SKIN AND NAIL INFECTIONS USING GERMICIDAL LIGHT

(75) Inventor: William E. Cumbie, Yorktown, VA (US)

(73) Assignee: Keraderm, LLC, Hampton, VA (US)

( * ) Notice: Subject to any disclaimer, the term of this patent is extended or adjusted under 35 U.S.C. 154(b) by 218 days.

(21) Appl. No.: 11/154,707

(22) Filed: Jun. 17, 2005

(65) Prior Publication Data

US 2006/0004425 A1 Jan. 5, 2006

Related U.S. Application Data

(63) Continuation-in-part of application No. 10/215,834, filed on Aug. 9, 2002, now Pat. No. 6,960,201.

(60) Provisional application No. 60/355,088, filed on Feb. 11, 2002.

(51) Int. Cl.
*A61N 5/06* (2006.01)

(52) U.S. Cl. .............................. 607/88; 607/89; 606/9; 128/898

(58) Field of Classification Search .................. 607/88, 607/89; 606/3, 9; 128/898
See application file for complete search history.

(56) References Cited

U.S. PATENT DOCUMENTS

| 1,183,949 | A |   | 5/1916  | Burdick |
| 1,510,080 | A |   | 9/1924  | Murphy |
| 1,702,028 | A |   | 2/1929  | Blanchard |
| 1,856,969 | A |   | 5/1932  | Reiter et al. |
| 2,165,449 | A |   | 7/1939  | Budd |
| 3,986,513 | A |   | 10/1976 | Stuhl |
| 4,246,905 | A |   | 1/1981  | Corth |
| 4,298,005 | A |   | 11/1981 | Mutzhas |
| 4,558,700 | A |   | 12/1985 | Mutzhas |
| 4,871,559 | A |   | 10/1989 | Dunn et al. |
| 4,909,254 | A |   | 3/1990  | Wilkinson |
| 4,910,942 | A |   | 3/1990  | Dunn et al. |
| 4,930,504 | A |   | 6/1990  | Diamantopoulos |
| 5,034,235 | A |   | 7/1991  | Dunn et al. |
| 5,344,433 | A |   | 9/1994  | Talmore |
| 5,871,522 | A |   | 2/1999  | Sentilles |
| 5,900,211 | A |   | 5/1999  | Dunn |
| 5,947,956 | A |   | 9/1999  | Karell |
| 6,042,603 | A | * | 3/2000  | Fisher et al. .................. 607/89 |
| 6,053,180 | A |   | 4/2000  | Kwan |
| 6,090,788 | A | * | 7/2000  | Lurie ........................... 514/23 |
| 6,129,893 | A |   | 10/2000 | Bolton |
| 6,165,170 | A | * | 12/2000 | Wynne et al. ................. 606/9 |
| 6,174,325 | B1 |  | 1/2001  | Eckhouse |
| 6,254,625 | B1 |  | 7/2001  | Rosenthal et al. |
| 6,264,836 | B1 |  | 7/2001  | Lantis |
| 6,264,888 | B1 |  | 7/2001  | Palestro et al. |
| 6,283,986 | B1 |  | 9/2001  | Johnson |
| 6,379,376 | B1 |  | 4/2002  | Lubert |
| 6,663,659 | B2 | * | 12/2003 | McDaniel ...................... 607/88 |
| 6,835,202 | B2 |  | 12/2004 | Harth et al. |
| 6,960,201 | B2 | * | 11/2005 | Cumbie ........................ 606/9 |
| 2002/0083535 | A1 |  | 7/2002  | Fraden |
| 2002/0183811 | A1 |  | 12/2002 | Irwin |
| 2003/0027186 | A1 |  | 2/2003  | Pierce |
| 2004/0236267 | A1 |  | 11/2004 | Pierce |
| 2005/0019256 | A1 |  | 1/2005  | Dobkine et al. |
| 2005/0242301 | A1 |  | 11/2005 | Pierce |
| 2005/0256552 | A1 |  | 11/2005 | White |
| 2005/0256553 | A1 |  | 11/2005 | Strisower |
| 2006/0079948 | A1 |  | 4/2006  | Dawson |
| 2006/0173515 | A1 | * | 8/2006  | Cumbie ........................ 607/88 |
| 2006/0212098 | A1 |  | 9/2006  | Demetriou |
| 2006/0241729 | A1 |  | 10/2006 | Dawson |

OTHER PUBLICATIONS

Moller, et.al. 'How Finsen's Lamp Cured Lupus Vulgaris', 2005. pp. 118-124, Photodermatology, Photoimmunology, and Photomedicine. Pub. by Blackwell Muskgaard, Copenhagen, Den.

Russell, 'Ultra-Violet Radiation and Actinotherapy', 1933. Cover, TOC and pp. 260-305 and 416-447. Pub. by E&S Livingstone, Edinburgh, Scotland.

Clayton, 'Electrotherapy and Actinotherapy', 1952. Cover, TOC, and pp. 312-362 and 410-429 Pub. by Baillere, Tindall, and Cox, London, England.

United Nations- World Health Organization, 'Summary of Env. Health Criteria 160', Undated. 8 pages, Pub. by WHO, Geneva, Switzerland.

U.S. Environmental Protection Agency, 'Manual of Alternative Disinfection', 1999. Chapter 8 (pp. 8-1 to 8-25). Published by USEPA, Washington D.C.

United Nations- World Health Organization, 'Env. Health Criteria 160', 1994. Table of Contents and Chapter 6 (Cellular and Molecular Studies). Pub. by WHO, Geneva, Switzerland.

FDA, 'Kinetics of Microbial Inactivation for Alternative Food Processing Technologies', 2000. 8 page summary. Pub. by FDA, Washington, DC.

Beckett, 'Modern Actinotherapy', 1955. Cover, TOC, and pp. 78-111. Published by William Helnemann, London, England.

(Continued)

*Primary Examiner*—A. Farah
(74) *Attorney, Agent, or Firm*—Merek, Blackmon & Voorhees, LLC

(57) ABSTRACT

A method of prevention and treatment of microbial infections that occur on, or just below, the skin and nails of a person consisting of electromagnetic radiation to inactivate the microbes thus rendering them harmless. The treatment consists of irradiating an area of the skin and nails for a period of time long enough to inactivate the organisms. Some additional features which are not integral to the treatment but increase the safety of the treatment include shielding of non-infected areas from irradiation and a cover to prevent damage to sight which may result from viewing the electromagnetic radiation.

54 Claims, 8 Drawing Sheets

OTHER PUBLICATIONS

Fluharty, et. al. 'The Discovery and Subsequent Research of Cryptosporidium Inactivation', Undated. 6 pages. Published by Calgon Corporation, Pittsburgh, PA.

Moss and Davies. 'Interrelationship of Repair Mechanisms in Ultraviolet Irradiated *Escherichia coli*', Oct. 1974. Journal of Bacteriology pp. 15-23. Pub. Am. Soc.of Microbio.

Smith. 'Scientific History of Kendric Smith', Undated. 39 pages. Published on the Internet.

Rudiger Hell, 'Sulfer Rich Proteins Involved in Stress Resistance'. 25 pages. The Heidelburg Institute of Plant Sciences, Univ. of Heidelburg, Germany.

Osbourne, 'Antimicrobial Phytoprotectants and Fungal Pathogens: A Commentary', 1999. Fungal Genetics and Biology, pp. 163-168. Salisbury Lab, Norwich, England.

National Biological Corporation, Derma-Wand Advertisement, 1999, 2 pages.

Wekhof, Alexander, "Disenfection with Flash Lamps", May 2000, p. 264-276.

Wekhof, Alexander, "Pulsed UV Disintegration (PUVD): a new sterilisation mechanism for packaging and borad medical hspital applications.", May 2000, p. 264-276.

* cited by examiner

PREVENTION AND TREATMENT OF SKIN AND NAIL INFECTIONS USING GERMICIDAL LIGHT

CROSS-REFERENCE TO RELATED APPLICATIONS

This application is a continuation in part of U.S. application Ser. No. 10/215,834, filed Aug. 9, 2002 now U.S. Pat. No. 6,960,201, issued Nov. 1, 2005, which claims the benefit of U.S. Provisional Application 60/355,088 with filing date of Feb. 11, 2002.

BACKGROUND

1. Field of Invention

This invention relates to preventing and treating skin and nail infections using germicidal radiation to inactivate and kill organisms that cause such infections.

2. Background of the Invention

The germicidal effects of certain types of light have been recognized for many years. As early as the late 1890's certain types of ultraviolet light were found to have a germicidal effect. However, the wavelengths of light found to be germicidal have very little power to penetrate which limited their usefulness in treating infections. The most germicidal band, labeled UVC and extending from 240 to 280 nm, is totally absorbed by the atmosphere before it reaches the Earth's surface. Published research indicates that UVC can only penetrate the skin about 0.1 mm. Although germicidal light was found useful to sterilize air or water and to treat hard surfaces such as laboratory benches, its lack of penetration made it appear unsuitable to treat skin and nail infections.

Niels Finsen received the 1903 Nobel Prize in Medicine for his discovery that light in the ultraviolet region could be used to treat skin tuberculosis, a very serious disease at that time. The treatment as described in the 1903 Nobel Prize acceptance speech consisted of concentrating the rays of the sun and eliminating its longer heat producing rays or using a carbon arc lamp. The skin is exposed for an hour or so until it becomes red and inflamed. This treatment was repeated as necessary until the skin scarred over and then later grew in clear. The treatment was described as having no unpleasant effects, but was expensive, and required constant supervision. The light used had a very low percentage of UVC and it was thought that the main effect of the light used was to stimulate the body's natural defenses. It was thought that germicidal light could not effectively penetrate the skin to treat the infection but that the main purpose of the light was to stimulate the body's natural defenses.

This type of treatment for skin tuberculosis and several other skin diseases continued through the 1950's but was eventually replaced by the use of antibiotics. Early use of ultraviolet light was much more of an art than a science. In the early 1900's science was just beginning to form its modern theory of the composition of light and the science of genetics was many decades off. Thus researchers did not have the theoretical knowledge of how germicidal light damages genetic material to guide them in their treatments.

Early practitioners of phototherapy for the treatment of skin infections were aware of the germicidal effects of light but did not think they contributed significantly to UV phototherapy. In *Ultra-Violet Radiation and Actinotherapy* (Russel, 1933) it was noted that 'Ultraviolet light is absorbed by the protoplasm of the organism, and in a culture, or on the surface of a wound, one bacterium will protect a second lying under it; so in a lesion like lupus very little beneficial therapeutic effect can be considered to be due to the bactericidal effects of the rays. It is due rather to the increased lymphocytosis in the part, and stimulation of cicatrisation.' (Russel, 1933, pg. 288). The text also notes that 'the absorption by the skin of very short wave-length, is very great, all rays shorter than 3000 angstroms [300 nm] being absorbed by a later of epidermis 0.1 mm in thickness' (Russel, 1933, pg. 272-273). The lamps which were used to treat skin infections had at least 95% of their energy emitted at wavelengths over 300 nm and thus had very little energy in wavelengths considered germicidal. This compares to modern low pressure mercury germicidal lamps where 95% of light is emitted at 254 nm—almost the exact opposite of earlier lamps used to treat skin disorders.

U.S. Pat. No. 1,856,969 by Reiter and Gabor in 1932 describes a type of phototherapy to modulate living tissue that was used as part of empirically based treatment of skin disorders. The patent describes the use of UV to stimulate the natural defenses of the body and includes a filter to prevent light less than 320 nm from reaching the skin since light below 320 nm was felt to be detrimental to treatment. This patent illustrates that most early UV therapy was focused on the stimulating effects of UV and not on its germicidal qualities since the wavelengths considered germicidal (less than 315 nm) were considered to be detrimental to treatment.

Treatment of skin diseases continued on an empirical basis through the 1950's with a multiplicity of units being produced each with different approximated guidelines of how to best use them for various disorders and infections. The empirical basis of treatment of these disorders was based on judiciously applying ultraviolet light to cause erythema (redness) to develop. The treatment was then adjusted to bring about various degrees of sunburn depending on the disorder being treated. Mild erythema (slight redness) was assigned a value of E-1 while the most sever erythema (blistering and third degree burns) was assigned an E-4. The most serious infections often merited a treatment bringing about an E-4 erythema for a sustained period. The induced erythema was thought to stimulate the body's defenses, particularly increasing the bactericidal ability of the blood. Although this was the most prevalent theory of why this treatment was efficacious there was no absolute consensus. The lack of consensus with regard to how this type of treatment worked and the large number of lamps that were being marketed in the first half of the twentieth century was probably bewildering to many doctors. Nevertheless, in the absence of modern antibiotics, even the empirical use of ultraviolet light to treat skin infections.

*Electrotherapy and Actinotherapy; A Textbook for Student Physiotherapists* authored by E. B. Clayton and published in 1952 ($2^{nd}$ edition) shows of the state of the art of phototherapy before use of modern antibiotics caused this form of treatment to lose favor. This 451 page textbook covers all aspects of phototherapy beginning with the theory, the type of equipment used, and treatment of various types including skin disorders. Portions of the treatment section for skin tuberculosis read as follows, "The Finsen-Lomholt water cooled carbon arc or the Kromayer lamp is employed. The latter has the disadvantage that its spectrum includes a quantity of abiotic rays which are not required and merely increase the superficial inflammation . . . . The initial exposure is commonly five times a fourth degree erythema." (pgs. 413-414). This extract of the book notes that abiotic (germicidal) light is not considered helpful for treatment. It also shows that dosages for treatment were based on empirically derived rules of thumb related to how severe the produced erythema was. Although almost 100 pages are devoted to describing various treatments there is no mention of dosage in terms of the amount of energy applied nor is there mention of any specific wavelengths.

Empirical use of ultraviolet light had a number of undesirable side effects including a wide spectrum of light including high amounts of UVB light now known to be carcinogenic. The relative amount of germicidal light was extremely low which made any possible benefit due to its inclusion very small and probably undetectable. Also, the cure rate was also much lower than can be expected with a well understood theory of how germicidal light inactivates organisms. Thus, when safer and more effective antibiotics were introduced in the 1950's the practice of empirically using ultraviolet light to treat skin infections was quickly abandoned by the medical profession in general. While ultraviolet light may still be used to empirically treat skin infections in isolated areas of the world its general use has been abandoned.

There appears to have been no application of the recent advances in genetics, air handling, and water and wastewater disinfection to transform the use of germicidal light to scientifically treat skin infections. The present invention combines these advances in other fields to develop a novel and unique approach to scientifically treat skin and nail infections in a manner that increases the efficacy of treatment while minimizes the side effects of such treatments.

It should be noted that there is no indication that this type of treatment was ever applied to treating nails. While the text discuss a number of different disorders affecting different parts of the body (including skin, nose, throat, anus, etc.) the mention of nails is not found in any text. This is understandable given the limited ability of nails to transmit light in the ultraviolet range and the fact that nail diseases in general are less life threatening than skin infections.

With the discovery of DNA and RNA in the 1950's and the subsequent development of the science of genetics, scientists discovered that each cell contained a highly sophisticated code to permit the cell to reproduce. Later, it was found that certain kinds of ultraviolet light could damage this genetic material and prevent a cell from reproducing. This knowledge was applied in many different fields including water and wastewater treatment (where it was used to disinfect water), to sterilize surfaces, and to sterilize air. However, it was not applied to treat skin infections. This was perhaps due to several reasons including the following:

The widespread knowledge that UV cannot penetrate deeply made it a less than ideal candidate to treat an infection that may not be totally on the surface of the skin. Since it is well documented that light less than 300 nm cannot penetrate below the first 0.1 mm of the epidermis, its penetrating power was thought insufficient to treat infections.

The old empirical use of UV light made use of lights of varying characteristics and strengths. It is likely that these lights cause some pain and tenderness due to their non-specificity. Also, since there was no knowledge of how the light cleared infections, it was applied in a broad manner and probably had significant side effects due to overdosing including cancer due to high level of carcinogenic UVB.

While Niels Finsen is cited as the founder of phototherapy by many authors, the industry has all but abandoned the use of ultraviolet light to treat infections and has instead concentrated on the visible and infrared part of the spectrum from 400 nm to 1000 nm. The invention disclosed in this application builds on Finsen's work and extends it in new and innovative ways by combining new knowledge of genetics and advances in the use of ultraviolet light to disinfect air and water. The combination of diverse knowledge that the invention builds on is not generally known to those skilled in the art of phototherapy and when this new knowledge is combined with the existing empirical base provided by Finsen and other early phototherapists, new and unobvious applications of this knowledge to prevent and treat skin and nail infections emerge.

The germicidal effects of electromagnetic radiation have been recognized for many years. Currently, germicidal radiation (also called germicidal light) is being used more frequently at water and wastewater treatment plants to render water-borne pathogens harmless. Additionally, germicidal light is used to sterilize and purify air, particularly in laboratories and medical establishments. It is also used to sterilize equipment at such establishments. Germicidal light has been used for several years to sterilize and disinfect food products and has also been used to sanitize the hands to prevent the spread of germs to other persons. Over the years a large body of knowledge concerning germicidal radiation has been developed but has not been systematically applied to address important problems with respect to treating skin and nail infections.

While germicidal light is not used by itself to treat skin and nail infections, certain types of light that are considered non-germicidal are frequently combined with other additional chemical compositions to treat existing psoriasis, rashes, and other non-infectious skin disorders. It is believed that this type of treatment, termed phototherapy, is effective because it has an immunosuppressive effect that permits the body to heal itself. Recently, lasers alone have been successfully used to treat psoriasis by clearing localized chronic plaque. Phototherapy is also used to treat jaundice which is also a non-infectious disorder. However, no method of using germicidal light alone has been discovered to successfully treat existing microbial infections nor has this type of light been used as a preventative treatment for infections.

Perceived Inability of Germicidal Light to Penetrate Skin and Nails

The main reason that germicidal light alone has not been used to prevent and treat skin and nail infections is that the most potent germicidal light is in the UVC range (240 nm to 300 nm) and this type of light cannot penetrate the skin and nails deeply. Significantly less than 1% of UVC light can penetrate nails or the deeper than 0.1 mm of skin (i.e. does not penetrate the epidermis).

UVB (280 nm 315 nm) while not generally considered germicidal also has some limited germicidal ability particularly in the 280 nm to 300 nm part of the spectrum. However, it also has limited penetrability. For example UVB it is estimated that less than 5% of light at 315 nm penetrates the epidermis (approx. 0.125 mm deep) or nails. The perceived inability of germicidal light to penetrate the skin and nails is one of the major reasons that this type of light has not been used to prevent and treat infections. If the light cannot penetrate skin or nails and reach the infectious organisms it is of no use for treating infections. However, it is this difference between no penetration and little penetration that the disclosed invention makes innovative and unobvious use of. Although less than 1% of UVC light can penetrate nails or can penetrate skin deeper than 100 mm, the less than 1% of light that is able to penetrate deeper is sufficient to prevent and treat skin and nail infections when applied properly.

Less than 8% of UVB at 315 mm can penetrate nails or skin deeper than 0.1 mm. This is much greater than the penetration ability of UVC, however, given its lower germicidal ability it does not appear to be as effective treatment for infections. Nevertheless, UVB can be used germicidally to treat infections if it is of sufficient strength or if it is accompanied by use of UVC light.

There is a large amount of literature that teaches that germicidal light cannot penetrate well. The Physics Society in its July 1998 paper titled "Ultraviolet Radiation and the Public Health" notes that "UVC, used in germicidal lamps, causes almost no damage because of its low penetration of the skin." INTERSUN, the global UV project sponsored by the United Nations indicates only 5% of UVC (at 254 nm) can penetrate to approximately a quarter of the depth of the epidermis and less than 1% can penetrate more than half the depth of the epidermis. Many other sources indicate that UVC cannot penetrate the skin or can do so only to a very limited depth. However, this depth is sufficient to treat infections since organisms are particularly susceptible to germicidal radiation. Also, with respect to nail infections, the additional radiation required to penetrate the nail is not harmful to the nail since it is composed of dead keratin.

UVC Dose Necessary to Inactivate Microbes

A second major reason the use of UV has not been contemplated are the relatively high doses necessary to kill some types of organisms. However, it has been found that it is not always necessary to kill organisms to render them harmless. It has been shown that organisms can be inactivated and rendered harmless using far less radiation than is necessary to kill them completely. Therefore, although its use as a treatment for has been overlooked in the past, electromagnetic radiation of sufficient strength can be used to treat human and animal infections.

There are several publications that note that organisms can be rendered harmless with less energy than is necessary to kill them. The inactivation of organisms by damaging RNA and DNA and preventing them from reproducing is a method used for disinfection of highly transparent potable water and is discussed in more detail in U.S. Pat. No. 6,129,893 to Bolton. The patent describes a method for preventing the replication of *Cryptosporidium parvum* using ultraviolet light. This patent indicates that ultraviolet light can inactivate bacteria (as measured by infectivity studies) at doses that are 3% to 10% of the dose necessary to actually kill the organisms (as measured by microscopic examination of ruptured membranes). The method of inactivation is described as damage to the DNA and RNA that prevents the organisms from replicating. Since organisms are not long-lived in themselves, they are unable to continue to cause infection if they are unable to replicate. This discovery is applied to the inactivation of a pathogen in drinking water to render it safe for consumption. However, the method is only to irradiate one type of organism and then only in highly transparent drinking water.

The EPA guidance manual on Alternate Disinfectants and Oxidants (April 1999) devotes Chapter 8 to a discussion of germicidal UV as a disinfectant for drinking water. The manual notes that a UV wavelength of 240 to 280 nm is highly absorbed by the RNA and DNA of a microorganism. The absorbance of UV by the organisms results in the damage to the organism's ability to reproduce. The damage is often caused by the dimerization of pyrimidine molecules. A dimer is a molecule consisting of two identical simpler molecules and dimerization is the process of linking the two molecules together. Dimerization of the pyrimidine molecules distorts the DNA helical structure. The EPA guidance manual also notes that the dose to inactivate 90% of most types of organisms is very low with a typical range of 2 to 6 mJ/cm$^2$. The manual notes that the germicidal radiation can be generated by a number of sources including a low pressure mercury lamp emitting at 254 nm, a medium pressure lamp emitting at 180 to 1370 nm, or lamps that emit at other wavelengths in a high intensity pulsed manner.

It should also be noted that it is not necessary to kill and inactivate all organisms in order to effect a cure for an infection. If a substantial amount of the organisms that have caused an infection are destroyed or rendered inactivated, the body's natural defenses will often work to clear the infection. Thus, doses of radiation necessary to effect a cure for an infection may be much lower than those necessary to sterilize an area by total destruction of all organisms.

While germicidal light is often said to inactivate organisms by damaging their genetic material and preventing them from reproducing, germicidal light can be applied in higher dosages to damage enough of the genetic material in the cell and prevent it from being able to properly function, thus leading to its death. For example, mRNA (messenger RNA) is used to control cellular processes, however, if it is severely damaged it cannot perform this function.

UVB as Germicidal Light

While UVB light has some germicidal qualities it is not often used to inactivate or kill organisms. Although approximately 10 times more UVB light can penetrate a given depth of skin and nails than UVC light, its lower germicidal ability does not make it as attractive a choice. UVB is also considered the band of UV that causes the most damage to skin, and is therefore considered more carcinogenic, and is thus avoided where possible. Additionally, UVB light is more difficult to generate than UVC light which is easily produced by a mercury vapor light (which is similar in manufacture to a fluorescent light). Nevertheless, UVB can be used germicidally and it may be desirable to use it particularly in conjunction with UVC light. The portion of the UVB range that adjoins the UVC range (UVB between 280 nm and 300 nm) is almost as germicidal as some bands of UVC. Practitioners of photobiology sometimes term UV light between 200 nm and 300 nm as 'Far UV' light (as opposed to 'Near UV' light which is often listed in the range of 300 to 400 nm). The current invention makes use of UVB for treatment of skin and nail infections even though most literature ignores its germicidal ability and teaches that UVB does not penetrate deeply. The invention also encompasses Near UV light in the range of 200 nm to 300 nm due to its germicidal nature.

Other Types of Germicidal Radiation

U.S. Pat. No. 5,900,211 shows that it is not only UVC and UVB that can be used to sterilize water and food. Dunn discusses the use of pulsed polychromatic light to inactivate organisms. Dunn uses much lower amounts of energy to inactivate an organism than would be necessary to destroy it by excessive heat. However, Dunn applies this technology only to the sterilization of food and other materials and does not contemplate it for treatment of skin or nail infections. This is presumably because of the perceived inability of the light to penetrate the skin or nails. (Dunn indicates that the effectiveness of the light is dependent on its ability to penetrate a medium effectively.)

Prior Art Using UVC to Kill and Inactivate Organisms

U.S. Pat. No. 6,254,625 shows an apparatus to sterilize hands to prevent the spread of infectious organisms. This apparatus makes use of light to sanitize the surface of the hands to prevent infections from spreading form person to person. In all of its embodiments it consists of at least two items. It makes use of light to kill organisms along with either additional light to recuperatively heal the skin that has been irradiated or the use of ozone to increase the efficiency of killing organisms. The recuperative healing light uses the phenomenon of photoreactivation whereby cells and organisms that have been damaged can repair the damage using such light of a different wavelength. The inclusion of this source of light as part of the apparatus indicates that the disease causing organisms are killed and not merely inactivated otherwise they too could repair damage by photoreactivation. Additionally, the patent does not contemplate the use of the apparatus to treat an infected area of the skin and it makes no mention of treating any infection of the nails using electromagnetic radiation. The apparatus relies on the use of ozone to kill any organisms under the nails or shielded by debris and notes incorrectly that UVC radiation will not penetrate the nail. Rosenthal appears to be unaware that germicidal UV can penetrate the skin and nails and is used to treat infections.

U.S. Pat. No. 6,283,986 discusses the use of UVC radiation to treat wounds. However, Johnson only applies radiation to open wounds, which can be readily exposed, and notes that "given the short wavelength of UVC, no penetration of the underlying tissue would be expected." The patent makes no mention of skin infections and mention of the nails is totally absent from the application although nail infections comprise a large part of total dermal infections. Possibly, the reason the patent only applies to wounds is that by their nature wounds are open and therefore capable of having their surfaces irradiated. It appears that Johnson is also unaware of the ability of germicidal radiation to penetrate the skin and nails.

It is the misconception that germicidal light cannot penetrate skin and nails which has in part prevented the discovery that germicidal radiation, including UVC, can indeed penetrate to a depth sufficient to be used successfully to treat skin and nail infections. While it is true that skin and nails will absorb a large percentage of UVC, enough can penetrate to successfully treat and prevent infections.

Nail Infections and Treatment

Nail infections are a particularly significant problem in the general population, affecting an estimated 5% to 15% of the overall population (approximately 15 to 45 million people). This percentage is significantly higher in the elderly age group and among athletes and other individuals who have high moisture in the area of their feet. Nail infections are often caused by fungus and this type of infection is termed *onychomycosis*. Currently, the preferred method for the prevention and treatment of skin and nail infections relies on application of topical medications or ingestion of medications. These medications are used to treat an existing infection, not for the prevention of an infection. Cost of treatment using medication can be between $600 and $1200 per course of treatment and can last three to six months. This is the amount of time it takes the medication to be incorporated into the nails. Another one to six months is then required for the nail to become free of infection. It should be noted that the cost noted above does not take into account doctors visits or diagnostic testing to determine if the patient can tolerate the medication (many medications can cause liver and other damage).

The problems associated with oral anti-fungal medications can be illustrated by several quotes from the clinical testing results for Itraconazole capsules (marketed under the trademark name SPORANOX® manufactured by Janssen Pharmaceutica, Inc.) which was the most prescribed antifungal in the U.S. in 1996. The success rate for treatment of *onychomycosis* of the toenail is reported as follows—"Results of these studies demonstrated mycological cure . . . in 54% of the patients. Thirty-five (35%) of patients were considered an overall success (mycologic cure plus clear or minimal nail involvement with significantly decreased signs) and 14% of patients demonstrated mycological cure (clearance of all signs, with or without residual nail deformity)." With respect to adverse reactions—"SPORANOX® has been associated with rare cases of serious hepatoxicity, including liver failure and death. Some of the cases had neither pre-existing liver disease nor a serious underlying medical condition." In a study of 602 patients treated for systemic fungal disease, "treatment was discontinued in 10.5% of the patients due to adverse events."

Although it is relatively rare, death is another serious side effect of oral antifungal medications. The two most popular antifungal medications used to treat nail infections were implicated in a total of 35 deaths in the U.S. between 1996 and 2001. This caused the FDA to issue a health advisory for these medications in May of 2001.

Although the currently preferred method of treating nail infections is the use of oral medication, there are several other treatments in use. There are several topical applications that are used to treat fungal infections of the nails. However, these have an even poorer success rate than oral medications and the infections tend to re-occur.

U.S. Pat. No. 6,090,788 to Lurie shows destruction of fungal infections of the nails by introducing a pigment into an infected area and then heating the pigment in the infected area with a laser in order to raise the temperature high enough to kill the organisms that have caused the infection by excessive heating. The energy listed in the preferred embodiments is from 5 to 15 J/cm$^2$ and it has a relatively long wavelength (generally 500 to 700 nm) in order to penetrate the nail. The high amount of energy and long wavelength of light is great enough to cause excessive heating of the surrounding area thus destroying the organism. However, such high energy levels also have undesirable effects on the surrounding tissue such as redness and swelling.

Lurie incorrectly notes that typical fungi do not have pigment and, therefore, cannot absorb light. However, the fact is that all cells will absorb light at a wavelength of between 240 and 280 nm since the DNA in the organism will absorb light at this wavelength. Also, Lurie is not cognizant of the fact that organisms can be inactivated at much lower doses than those necessary to destroy them by excessive heat. Due to the complicated nature of the treatment, U.S. Pat. No. 6,090,788 is proposed as a method to treat an infection, not to prevent one.

Lurie also notes that the light he uses for treatment must easily penetrate the skin which is something that UV does not do. Thus it would not be a natural extension of Lurie's treatment to use UV light to directly treat nail infections.

Lurie notes "there is a widely recognized need for, and it would be highly advantageous to have, a phototherapy method for treating skin and nail pathogens and a pharmaceutical composition to effect same." It may be added that there is even a greater need to treat skin and nail infections using germicidal radiation only, particularly if said radiation could be effective at a much lower dose and not have the side effects associated with high energy lasers.

OBJECTS AND ADVANTAGES

Accordingly, several objects and advantages of the invention are:
 a) A method to treat the infected area directly thus eliminating the need to use oral medications that affect the entire body, may have serious side effects (including death), and have only a limited success rate for treating infections.
 b) A means to treat the infected area using a very small number of treatments (one to perhaps a dozen) over a short period of time (generally less than one month) as opposed to the need to ingest oral medication periodically for three months or more.
 c) A means to treat an infection much more cost effectively that the current cost of $600 to $1200 per course of treatment plus the additional costs of monitoring for side effects, etc.
 d) A means to treat an infection in much less time (generally less than a month) as opposed to having to wait three to six months for the medication to take effect.
 e) A means, which treats the infection using a minimal amount of radiation to inactivate the organism instead of radiation treatments using a large amount of energy to destroy an infection by excessive heat, thus greatly reducing the possibility of complication arising from using excessive amounts of energy and limiting the amount of potentially carcinogenic radiation that may need to be applied to effect a cure.
 f) A means to directly treat infections using radiation without first having to introduce an artificial pigment into the area about to be treated, saving time, cost, and eliminating the chance of side effects resulting from inducing the pigment.
 g) A means to prevent infections before they become established, by limiting costs, potential side effects, and the long length of time it takes to act.
 h) A means to prevent infections before they become established infections which is particularly valuable to those who are predisposed to infections or persons that such infections pose a significant threat.
 i) A device to accomplish the methods and means of preventing and treating skin and nail infections.

Still further objects and advantages will become apparent from a consideration of the ensuing description and drawing.

SUMMARY OF INVENTION

The invention, a method, means, and device to prevent and treat skin and nail infections, uses germicidal light to inactivate and/or kill the organisms that cause infections. The method of treatment consists of irradiating the portion of skin and nail to be treated using electromagnetic radiation of a germicidal nature. The method utilizes a previously unrecognized ability of germicidal light to penetrate the skin and nails sufficiently to successfully treat and prevent infections. Said electromagnetic radiation damages the organisms that cause skin and nail infections and disables their ability to replicate. Without the ability to replicate the organism cannot continue to infest the skin and nails. The infection is thereby prevented if it has not yet begun and it is cured if the infection already exists. Said invention is also referred to as "method to treat infections" in this application. The device disclosed is that necessary to execute the method described in this application.

BRIEF DESCRIPTION OF DRAWINGS—FIGS. 1-10

DETAILED DESCRIPTION OF INVENTION

Figure 1:
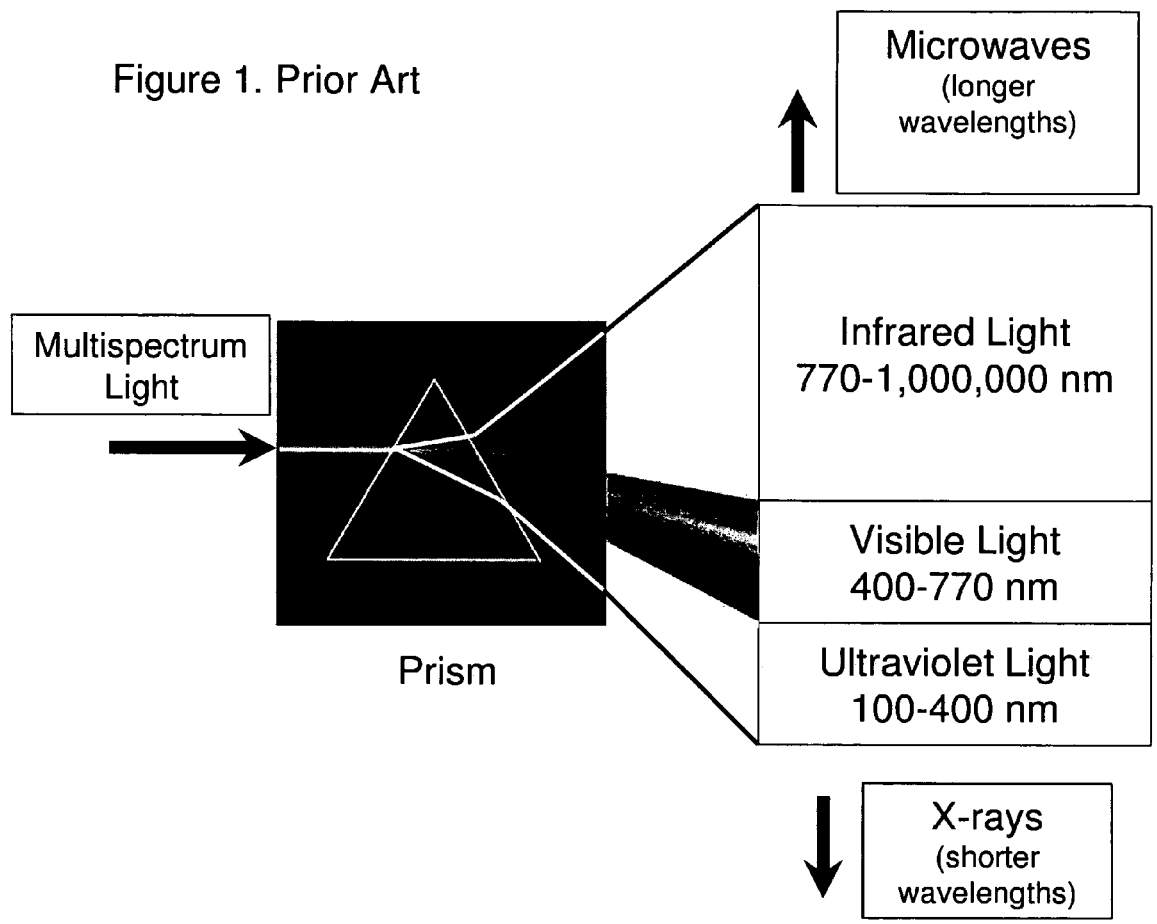
FIG. 1 is a diagram showing Light passed through a prism with light split and showing UV and Infrared.

Why Germicidal Light has not been Used Before to Treat Skin and Nail Infections

The germicidal effects of electromagnetic radiation have been recognized for many years. However, the germicidal effects of electromagnetic radiation have not been recognized as a method for the prevention and treatment of skin and nail infections.

While UV light was used in the first half of the twentieth century to treat skin diseases, the primary range of the light was the UVA range and to the lesser extent the UVB range. The UVC range was known to be germicidal during that time period, although how it exerted its germicidal effect was unknown. There was no thought of using the primary germicidal range of UV to treat skin and nail infections because the literature taught that such light could not penetrate below 0.1 mm. Thus the benefit attributed to UV light to heal infections was not primarily germicidal. In fact one text explains the biological effect of germicidal radiation as follows, 'Ultraviolet light is absorbed by the protoplasm of the organism, and in a culture, or on the surface of a wound, one bacterium will protect a second lying under it; so in a lesion like lupus very little beneficial therapeutic effect can be considered to be due to the bactericidal effects of the rays. It is due rather to the increased lymphocytosis in the part, and stimulation of cicatrisation.' (Russel, 1993, pg. 288). This perception that germicidal light could not penetrate sufficiently to be effective caused researchers to concentrate on the longer ranges of UV (above 315 nm) instead of the part of the band considered germicidal—primarily light below 315 nm.

Additionally, phototherapy in the first half of the twentieth century was primarily an empirical art. There were a large number of different kinds of lamps in the UV and non-UV range and their multiplicity prevented standardization of applied dosages. Instead, approximate exposure times were given for irradiation for an approximate length of minutes at an approximate distance. These distances and times were very approximate and depended on the type of lamp (each having different spectral characteristics) and how long the lamp had been in service since their output declined rapidly with use. One very detailed text on this type of treatment ("Ultraviolet Radiation and Actinotherapy" by E. H. Russel and W. K. Russel, 1933, 748 pages) has no mention of dosages to be applied in terms of energy such as Joules or Watt-seconds per area treated but relies solely on rule of thumb application rates.

There are several possible reasons why UVC was not given an adequate trial as a treatment for skin and nail infections:

First, it is commonly known that wavelengths less than about 315 nm cannot easily penetrate nails. Based on experience and limited testing of the penetration of 254 nm through human nail plates, less and 1% and perhaps as little as 0.001% (1/10,000th) of 254 nm light penetrates through a typical nail plate. However, it is important to recognize that fungi are mainly in the nail plate, and that UVC is so easily generated and so well tolerated that even an attenuation of 10,000 does not preclude effective treatment. For example, fungi are killed in a fraction of one second of exposure to a small UVC lamp. Multiplying this fraction of a second by 10,000 results in an exposure time in the range of 10 to 100 minutes of exposure time, i.e. a practical treatment time. Additionally, stronger UVC lamps are available which can further reduce necessary exposure times. Of particular importance also are lasers which can be tuned to a precise wavelength of light focused on the area of infection and which can deliver high doses of coherent light that can better penetrate skin, nails, and the infections themselves.

A second reason that UVC therapy has not been tried may be a misunderstanding of the dose required to effect a cure. It is not necessary to kill an organism to prevent it from sustaining an infection. It is possible to inactivate an organism by damaging its genetic material sufficiently to prevent it from being able to reproduce. Extensive studies of the dosage of UVC necessary to inactivate pathogenic organisms in drinking water indicate that often only 3% to 5% of the energy necessary to kill a particular organism (as measured by rupture of an organism's membrane) will cause it to be inactivated (as measured by infectivity studies) and unable to sustain an infection. Since this research has been conducted in a non-medical field it is not general knowledge in the community of researchers most likely to investigate treatment of infected nails. Many bacteria experience a 2 log inactivation (99%) at a dose of 1 to 12 mj/cm2 which is an achievable dosage even taking into account a low skin and nail transmissivity rate.

A third reason that phototherapy with UVC has not been pursued is that few people other than a mammalian photobiologist appreciate how well UVC exposure is tolerated by human skin. It is well known that the UVC dose causing a minimal (pink) sunburn is substantially less than that for UVB. This minimal sunburn dose is ample for germicidal effect on superficial organisms. Much less well known, is the fact that human skin tolerates hundreds of times this minimal dose very well. Thus large doses of germicidal radiation can be safely applied with the high doses being capable of offsetting the low penetration rate of UVC, Finally, many investigators may not recognize that it is likely that dermatophytes, the major cause of nail infections and some skin infections, are quite sensitive to UVC. The organisms are adapted to living without UV exposure. Moreover, UVC is filtered by the ozone layer and is not present in nature on the earth surface. Thus these organisms may lack the capability to repair damage to their genetic materials caused by exposure to UVC and may also be more sensitive than most bacteria.

These reasons also apply to the treatment of skin infections. However, it is the treatment of nail infections that is a particular problem since it is very difficult to treat such infections with the nail shielding the organisms which cause the infections.

Overview of UV Light

Ultraviolet light has a shorter wavelength than visible light as can be seen in FIG. 1.

Ultraviolet light is commonly broken down into three ranges labeled UVA (315 nm to 400 nm), UVB (280 nm to 315 nm), and UVC (100 nm to 280 nm).

Figure 2:
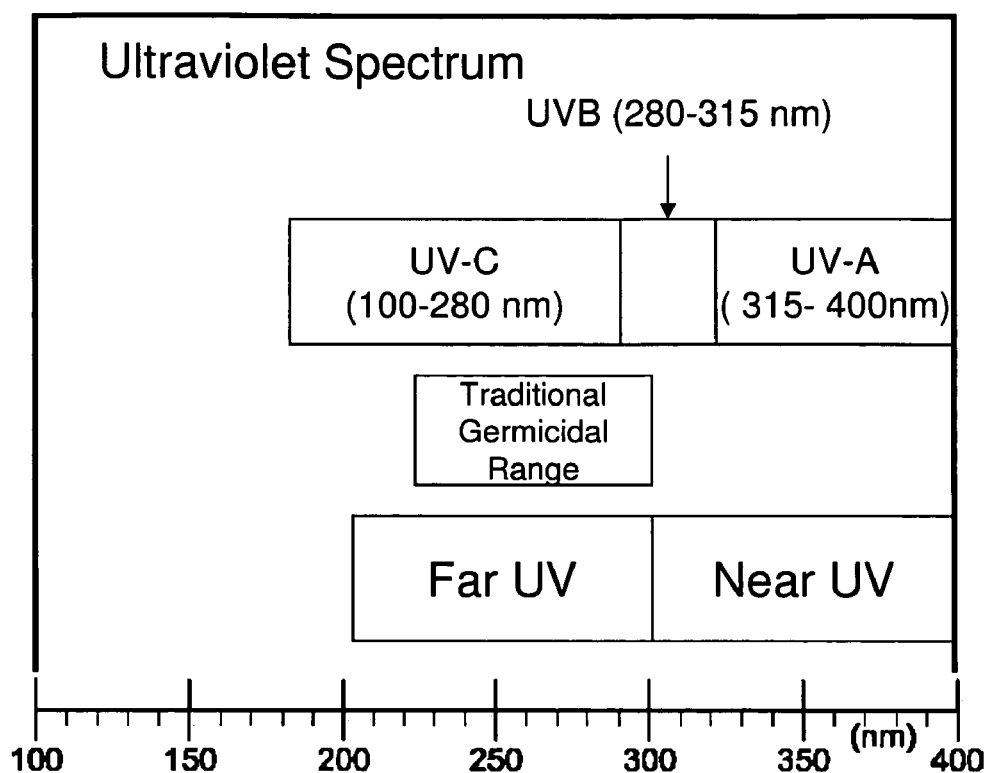
FIG. 2 is a chart showing the Divisions of Ultraviolet light (UVA, UVB, UVC, Far UV, and Near UV).

Another common division of UV light is Far UV (100 nm to 300 nm) and Near UV (300 to 400 nm). These ranges are graphically illustrated in FIG. 2.

Each light range has different effects on skin and organisms. UVA is the most commonly used light range for tanning. It is also the wavelength use for 'black lights' which fluoresce. UVA is also a light range commonly used for phototherapy of psoriasis in conjunction with photoactive agents.

UVB is considered the most destructive wavelength with respect to the skin and also the most carcinogenic. The amount of UVB emitted by tanning bulbs is regulated by the FDA due to its carcinogenicity. Nevertheless, 308 nm light (in the high range of the UVB range) has been successfully used to treat psoriasis. It appears that this autoimmune disorder responds well to this wavelength and its beneficial effect appears to outweigh its potential carcinogenicity.

UVC is the shortest wavelength and it generally has the least effect since it is easily absorbed and does not penetrate any media well. Since it is absorbed by the air, none of the UVC light emitted from the Sun reaches the surface of the earth. It does not penetrate the skin deeply and it has not been used in the treatment of skin disorders due to its low ability to penetrate the skin. However, UVC has the most germicidal effect organisms. If these organisms are suspended in the air or are on the surface of an object, UVC light can be used to kill and inactivate them. Again, due to its limited penetrability UVC has not been used to treat skin and nail infections since it was assumed that enough light would not penetrate to make treatment effective.

Figure 3:
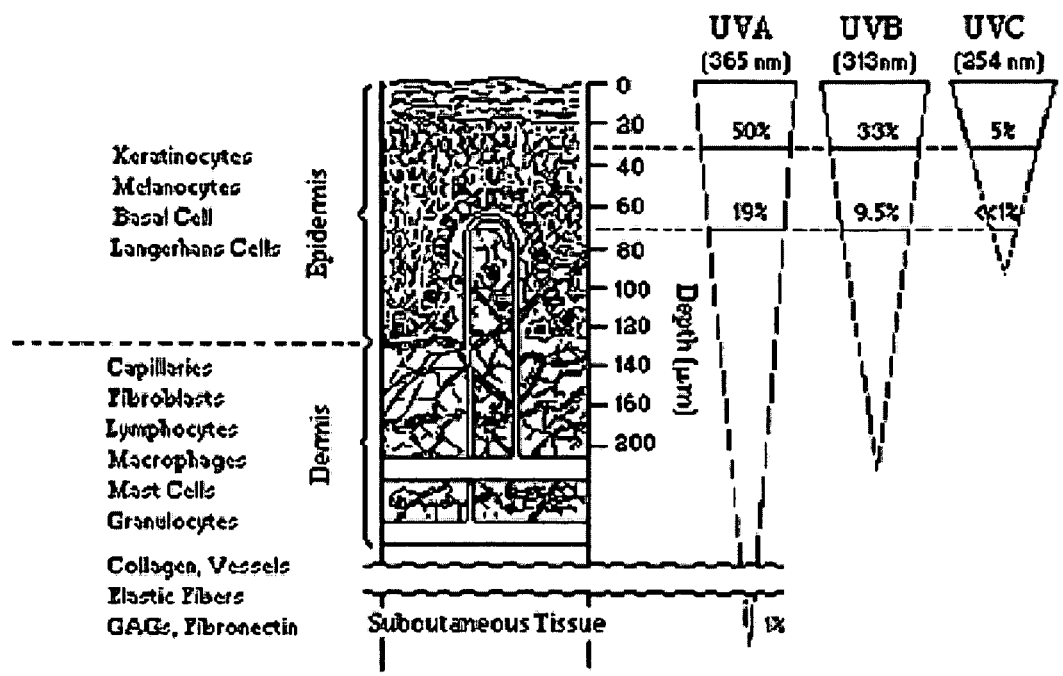
FIG. 3 is a diagram showing the Depth of penetration of Ultraviolet through skin.

FIG. 3 shows the various depths that UV will penetrate the skin. This figure is reproduced from the report titled Ultraviolet Radiation (Environmental Health Criteria: 160, published by the World Health Organization in 1994. ISBN 92 4 157160 8. This report is referenced in this report as 'UV Radiation, 1994'). The figure was numbered 4.1 in the text. This figure shows that while UVA light penetrates deeply into the epidermis and dermis, UVB light has much less ability to penetrate, and UVC can only penetrate part of the epidermis. At a depth of 75 um, 20 times more UVA light at 365 nm penetrates than UVC at 254 nm. This is why UVC has not been used to treat skin and nail infections.

However, low penetration is not the same as no penetration and the invented treatment relies on the fact that even a small amount of penetration can be used to successfully prevent and treat infections. UVC is so well tolerated by the skin and nails that it is possible to apply large enough doses that sufficient germicidal light penetrates deeply enough to prevent and treat skin and nail infections.

Germicidal light is a specific composition of matter composed of photons vibrating at specific wavelengths. It is the specific wavelengths of these photons that permit the light to interact with the biomolecules in the genetic material of the cells. During this interaction the light causes these biomolecules to deform and crosslink in a manner that prevents the cells from being able to replicate properly.

How UV Light Affects Cells and Organisms

Figure 4:
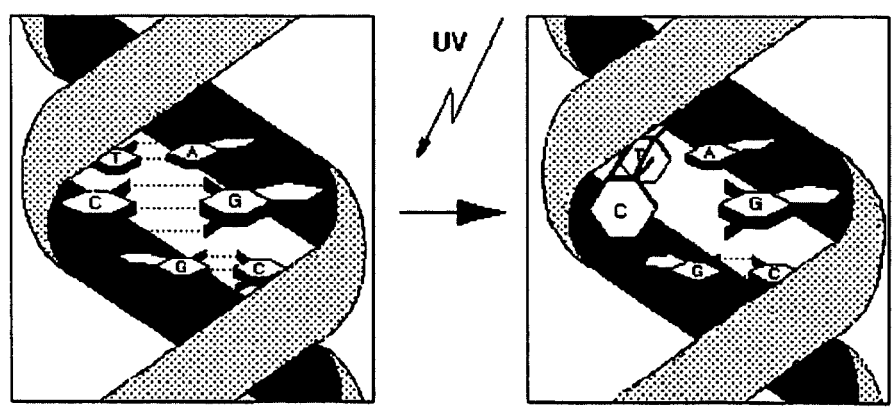
FIG. 4 is a diagram showing the Formation of pyrimidine dimers (crosslinking) in DNA cause by Ultraviolet light.

As discussed in a UV text (UV Radiation, 1994), UV light effects cells and organisms by a biomolecule as it absorbs a photon and produces an excited state which elevates the energy level of the absorbing molecule. The primary products of this interaction are reactive species or free radicals. DNA is the most critical target for damage by UVB and UVC radiation. While numerous types of UV induced DNA damage have been observed, the most significant reaction is the formation of cyclobutane-type pyramidine dimers as shown in FIG. 4 (reproduced from FIG. 6.1, UV Radiation, 1994).

Figure 5:
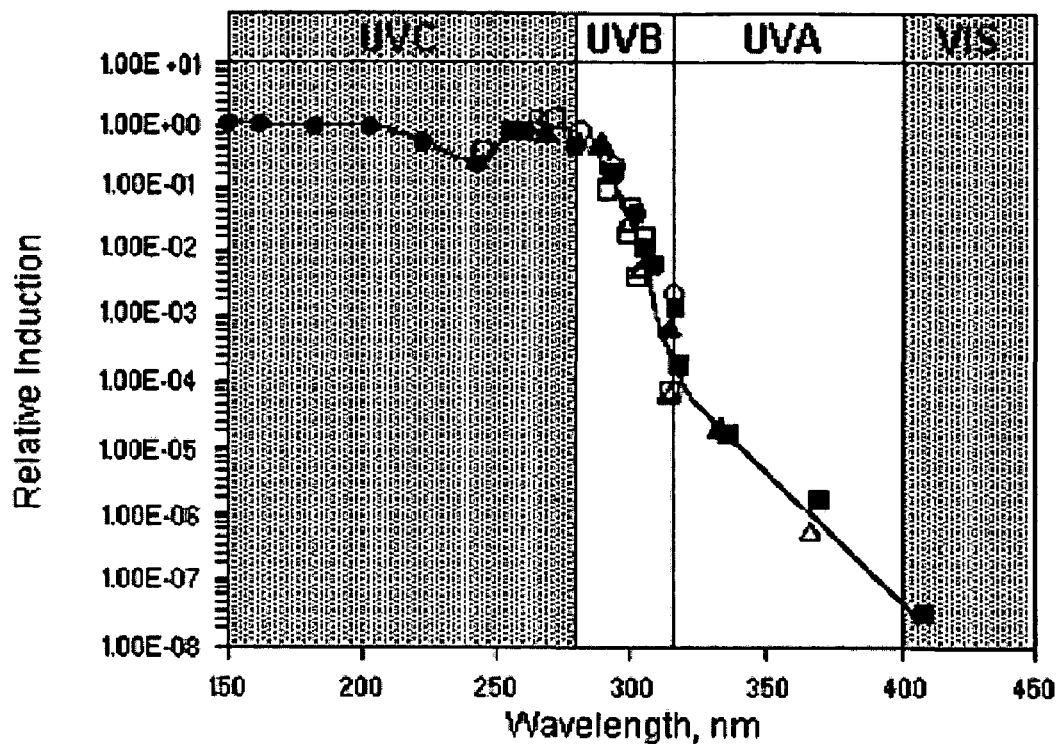
FIG. 5 is a chart showing the relative effectiveness of various wavelengths on pyrimidine dimerization (crosslinking) of DNA.

The formation of pyrimidine dimers is the most significant form of UV induced damage to cells and organisms and occurs primarily in the UVB and UVC ranges. It is especially strong in the UVC range and peaks at 260 nm. FIG. 5 below (reproduced from FIG. 6.2, UV Radiation, 1994). This figure clearly illustrates that outside the UVC and UVB range a significant amount of pyrimidine dimers do not form. For example, it takes approximately 100,000 times the dose of UVA light at 320 nm to form a pyrimidine dimer than it does with UVC light at 260 nm. This illustrates why UVC has such a potent germicidal effect compared with other wavelengths of light.

Figure 6:
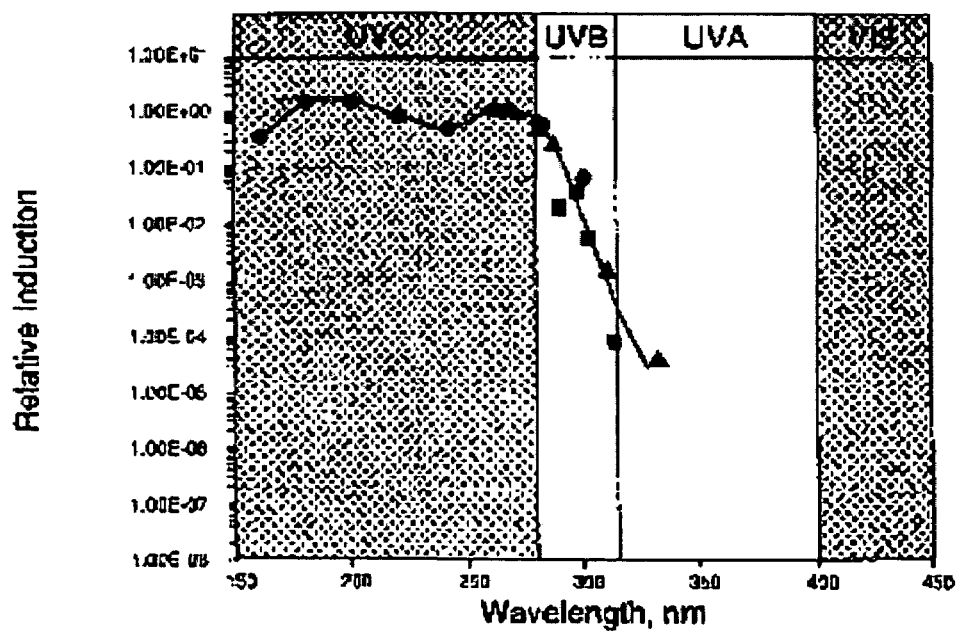
FIG. 6 is a chart Action spectra showing relative effectiveness of pyrimidine (6-4) pyrimidone adduct formation of DNA at various wavelengths.

A second type of pyrimidine dimer formed by UV is the thy (6-4) pyo photoproduct. This dimer also contributes to UVC's ability to damage the DNA of an organism. FIG. 6 shows the effectiveness of various wavelengths of light to form the 6-4 pyrimidine dimer.

Crosslinking of DNA prevents an organism or cell from replicating properly. DNA is a double helix that 'unzips' to provide a template for the cell to reproduce. Crosslinking of the DNA is analogous to a kink in a zipper that prevents it from unzipping properly. When the DNA is unable to form a template due to crosslinking the organism cannot reproduce properly and thus cannot sustain an infection. This type of inactivation of an organism by damaging its genetic material and preventing it from reproducing will be defined antigenosis for the purposes of this application. Processes that induce this antigenosis will be referred to as 'antigenotic.'

Because UV is absorbed by nucleic acids it also has the ability to damage additional functions of a cell or organism. Although this damage is less than that caused to DNA, if it is in sufficient quantity it can inactivate or even kill an organism. This damage is not caused by excessive heat but results from additional radiation damage to the organism such as damage to the RNA of an organism. Since RNA is used as a messenger within a cell, its destruction will result in the cell being effectively destroyed even before it eventually dies from damage to its DNA. Thus, in addition to inactivating and organism by damaging its DNA with UV, it is possible to destroy an organism with high doses of UV by disrupting its cellular processes. It may take 10 to 100 times the inactivation dose to actually kill the organism immediately instead of just damaging its ability to reproduce, however, due to the low heat generating ability of UV, this dose can be administered without causing excessive heating. Destruction of an organism in this way by damaging its genetic material and preventing it from reproducing will be referred to as 'geneticide.' It should be noted that although damage to the genetic material of a cell is the major cause of geneticide other processes can contribute to this process which are not directly genetic such as destruction of mRNA and the rupture of cell membranes.

Organism Destruction by Excessive Heat

Destruction by excessive heat is a different method used to kill organisms than irradiation by UV. Excessive heating to kill and organism relies on heat's ability to denature proteins in a cell. Denaturing of proteins by excessive heat causes the secondary, tertiary, or quaternary structure of proteins to unfold so that the protein's original properties, especially their biological activities, are diminished or eliminated. For example, an enzyme when it is subjected to high levels of heat unfolds and is no longer able to catalyze reactions. Destruction of an organism in this manner by excessive heat will be referred to as thermocide. A classic example of thermocide caused by the denaturing of protein by excessive heat is the boiling of an egg. The heat causes the protein albumin to denature and change from a clear liquid to a white solid. This example also illustrates the generally irreversible nature heat denaturization of protein since there is nothing that can be done to the white of the egg to reverse the process.

Most unicellular organisms contain in the range of 50% protein and less than 5% DNA (for example *E. coli* contains about 55% protein and about 3% DNA). Destroying an organism by adding excessive heat to denature proteins (thermocide) in general is thus relatively easy if enough heat is added. This excessive heat will effectively denature approximately half of the organism and this massive destruction will effectively destroy the cell. Targeting the destruction of the genetic material (geneticide) is a more precise means of inactivating an organism.

Distinction Between Thermocide (Denaturization Caused by Excessive Heat) and Geneticide (Destroying an Organism by Damaging Genetic Material)

Thermocide or destruction by excessive heat relies on denaturing proteins by applying large amounts of thermal energy while geneticide uses UV to destroy an organism using precise radiation to specifically target the genetic material of an organism. Geneticide or destroying an organism by damaging its genetic material can be accomplished by the use of UV irradiation and does not generate excessive heat and therefore requires significantly less thermal energy than thermocide.

For example, Lurie (U.S. Pat. No. 6,090,788, column 12, line 5) notes that yeast can be destroyed by applying excessive heat at a dosage of 5 to 10 $J/cm^2$ with a laser using 632 nm light. However, the inactivation dose for 99.9% destruction of common yeast is listed as approximately 0.01 $J/cm^2$ in the inactivation charts provided by Atlantic UV which is 500 times less energy. It should also be noted that even at the same dosage of UV there would be much less heating of the skin or nails since UVC at 254 nm only penetrates to 100 um while 632 nm light penetrates 10,000 um-100 times deeper. The greater depth of light penetration of the 632 nm generates significantly more heat than 254 nm light at the same energy. Thus the difference in heat generated to kill yeast using a 632 nm laser is significantly more than 500 times that generated to kill yeast using UVC light at 254 nm.

Damage of the genetic material of an organism can cause it to die by apoptosis, which is a term generally used in biology and is defined as the programmed death of an organism. Apoptosis occurs when an organism sustains enough damage that it cannot continue to function or it is damaged so that it cannot reproduce. When an organism receives this amount of damage it self-initiates the process of apoptosis which results in the ultimate disintegration of the organism. Apoptosis is different from necrosis the latter being a term generally used in biology and applied to a cell destroyed by outside forces such as the application of excessive heat. Irradiation of an organism can destroy an organism by both apoptosis (causing damage to the genetic material of an organism and causing it to initiate its own destruction) and by necrosis (by overwhelming the cell by damaging its genetic material in a way that it can no longer function effectively) while the addition of excessive heat must rely solely on necrosis.

Several analogies that may serve to illustrate the difference between destruction by excessive heat and destruction by radiation damage due to UV more clearly are listed below:

Destroying an organism by geneticide using UV is analogous to targeting a cell with a precise bullet (UVC radiation) instead of using a napalm bomb to destroy it (thermocide or destruction by excessive heat)

Destroying an organism by geneticide using UV is similar to sending in a special forces team to destroy a specific installation (the genetic material of a cell) instead of saturation bombing of an area (thermocide or destruction by excessive heat).

Summary of Treatments of Infected Nails

Figure 7:
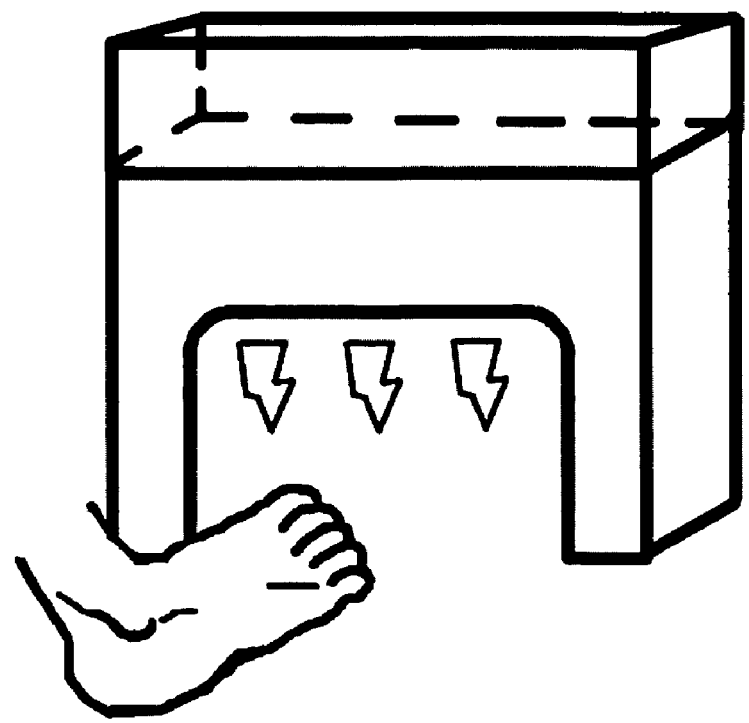
FIG. 7 is an environmental perspective of the invention for treating nail infection or disorder.

Treatment can be illustrated by the application of the invention to four infected nails. Germicidal light was generated using a low pressure mercury lamp of which approximately 95% of its light was emitted at a wavelength of 253.7 nm. This is illustrated in FIG. 7.

The dosage of UVC light was conservatively applied in order to ensure that the National Institute for Occupational Safety and Health (NIOSH) guidelines for daily irradiation of skin were not exceeded. The skin surrounding the nails was fully protected from the UVC irradiation by shielding. Preliminary transmissivity measurements on several healthy nails indicated that approximately 0.01% to 0.03% of UV 254 penetrates a healthy nail. Due to the limited test data it was assumed that 0.05% of UV 254 penetrated the nails. Total irradiation of the skin under the nail was limited to less than 6 mj/cm$^2$, the NIOSH standard for daily exposure. However, it should be noted that this guideline is very conservative and it is possible to treat infections using a much higher dose without generating significant side effects.

Summary of Testing and Results of Treatment of Infected Nails

The table below summarizes the results of testing on four nails tested:

| Nail No. | No. of Exposures | Average Dose per Exposure (mj/cm$^2$) | Total Dose (mj/cm$^2$) | Total Effective Dose (0.05% penetration) (mj/cm$^2$) | Effect on nail |
|---|---|---|---|---|---|
| 1 | 8 | 44.5 | 356 | 0.2 | Complete Cure |
| 2 | 7 | 319 | 2,233 | 1.1 | Some Improvement |
| 3 | 4 | 573 | 4,583 | 2.3 | Moderate Improvement |
| 4 | 4 | 573 | 4,583 | 2.3 | Major Improvement |

The success of treatment at the dosages of UV254 administered indicate that the organisms that cause onychomycosis are more sensitive or have a similar sensitivity to UV254 as bacteria, many of which exhibit two log (99%) inactivation in the range of 1 to 12 mj/cm$^2$.

A brief summary of each nail, irradiations, and the results of irradiation is included below.

Nail 1—Large toe nail had an aggressive fungal infection that spread rapidly. Nail was treated in several sessions over three months. Nail grew out clear. However, after one year there may have been a recurrence of the infection. Nail was treated again and grew out clear.

Nail 2—Large toe nail had moderate to severe onychomycosis. Nail had been removed several years earlier. However, the nail regrew and the infection was reestablished causing pain when shoes were worn. The nail showed moderate improvement and the pain associated with the infection was alleviated. However, the nail did not fully clear nine months after treatment.

Nail 3—Large toe nail had severe onychomycosis with erosion of skin at base of nail. Nail had been removed several times and person had used two different types of oral medications (at a cost of more than $1,000) with no improvement. Person had not used medication for fungal infection for several years before treatment. Less than three months after treatment the nail showed significant improvement. The skin at the base of the nail has regrown and new nail at the base of the nail is growing in much clearer. Most of the dark material under the nail has been eradicated.

Nail 4—Large toe nail had severe onychomycosis. Nail had been removed several times and person had used two different types of oral medications (at a cost of more than $1,000) with no improvement. The person had not used any medication for fungal infections for several years prior to irradiation. Less than three months after irradiation the nail shows significant improvement. After one year, the base of the nail is growing in almost clear and most of the dark areas under the nail are eradicated.

Discussion of Treatment

Results have been exceptional given the limited amount of data and the conservative application of germicidal light used during treatment. When the first two nails were treated it was assumed that 10% of the germicidal light penetrated the nail. Subsequent discussions and literature search indicated that this was too high and a value of 2% was used. Later preliminary testing with a UV meter indicated that actual light penetration was between 0.01 and 0.03%. Therefore, the amount of light used to treat nails 4 and 5 was increased.

Summary—Of the four nails treated, one of the nails exhibited complete cure, one nail has exhibited moderate improvement, and two nails have shown very significant improvement but have small areas which require additional treatment. Given that fungal infections do not clear by themselves and the difficulty in establishing the exact dose necessary for complete inactivation of an organism the initial results indicate significant efficacy. The data also suggest that a higher dose of light at 254 nm can be easily tolerated and would improve the efficacy of the treatment. It is estimated that doses of 10 to 20 J may be easily tolerated and that a series of 6 to 12 such treatments would cure a majority of nail infections. Since the nail itself is composed of dead keratin it is also possible that much higher doses of UVC light may be applied to the nails on the order of 100 J or more without significantly affecting the person being treated.

Illustrations of Treatment of Skin and Nail Infections

FIG. 7 shows the invention being used to treat a nail infection such as an infection caused by a dermaphyte such as *T. rubrum*. The invention may also be used to treat a nail disorder such as psoriasis of the nail.

Figure 8:
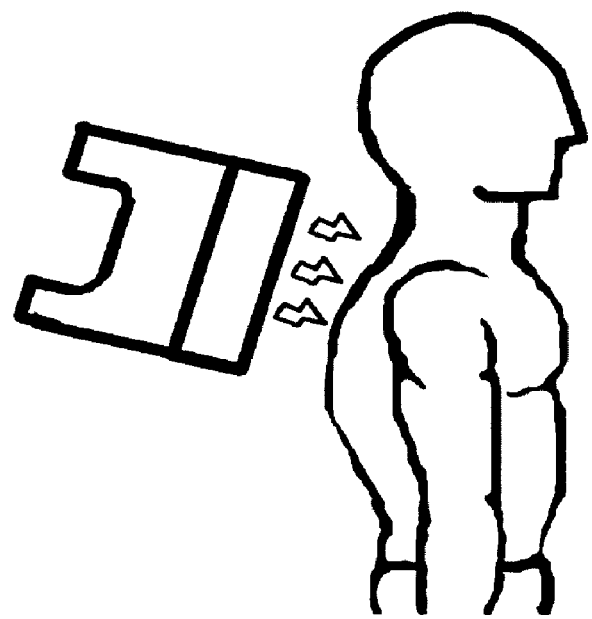
FIG. 8 is an environmental perspective of the invention for use in treating skin infection such as acne.

FIG. 8 shows the invention being used to treat a skin infection such as an outbreak of acne caused by *acne vulgaris*.

Figure 9:
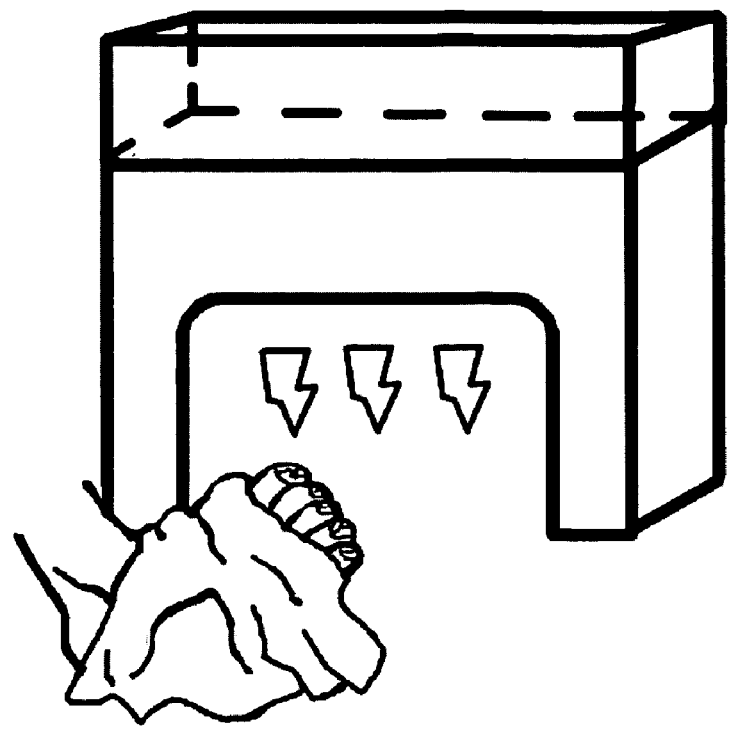
FIG. 9 is an environmental perspective of the invention for use in preventing nail infection.

FIG. 9 shows the invention being used to prevent a nail infection by irradiating the nail and killing any organisms before they can establish an infection.

Figure 10:
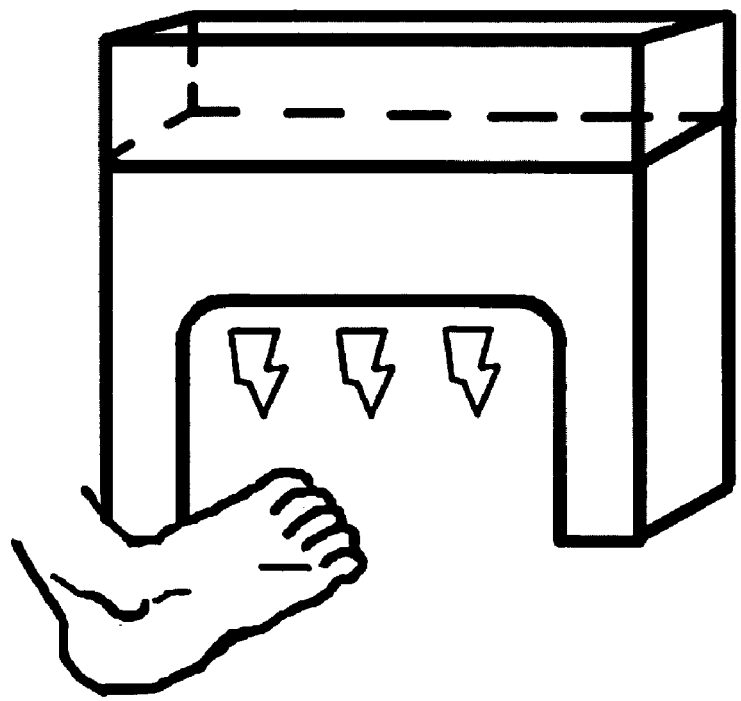
FIG. 10 is an environmental perspective of the invention for use in preventing a skin infection such as athletes foot.

FIG. 10 shows the invention being used to prevent a skin infection such as athletes foot by irradiating the skin and killing any organisms before they can establish an infection.

Figure 11:
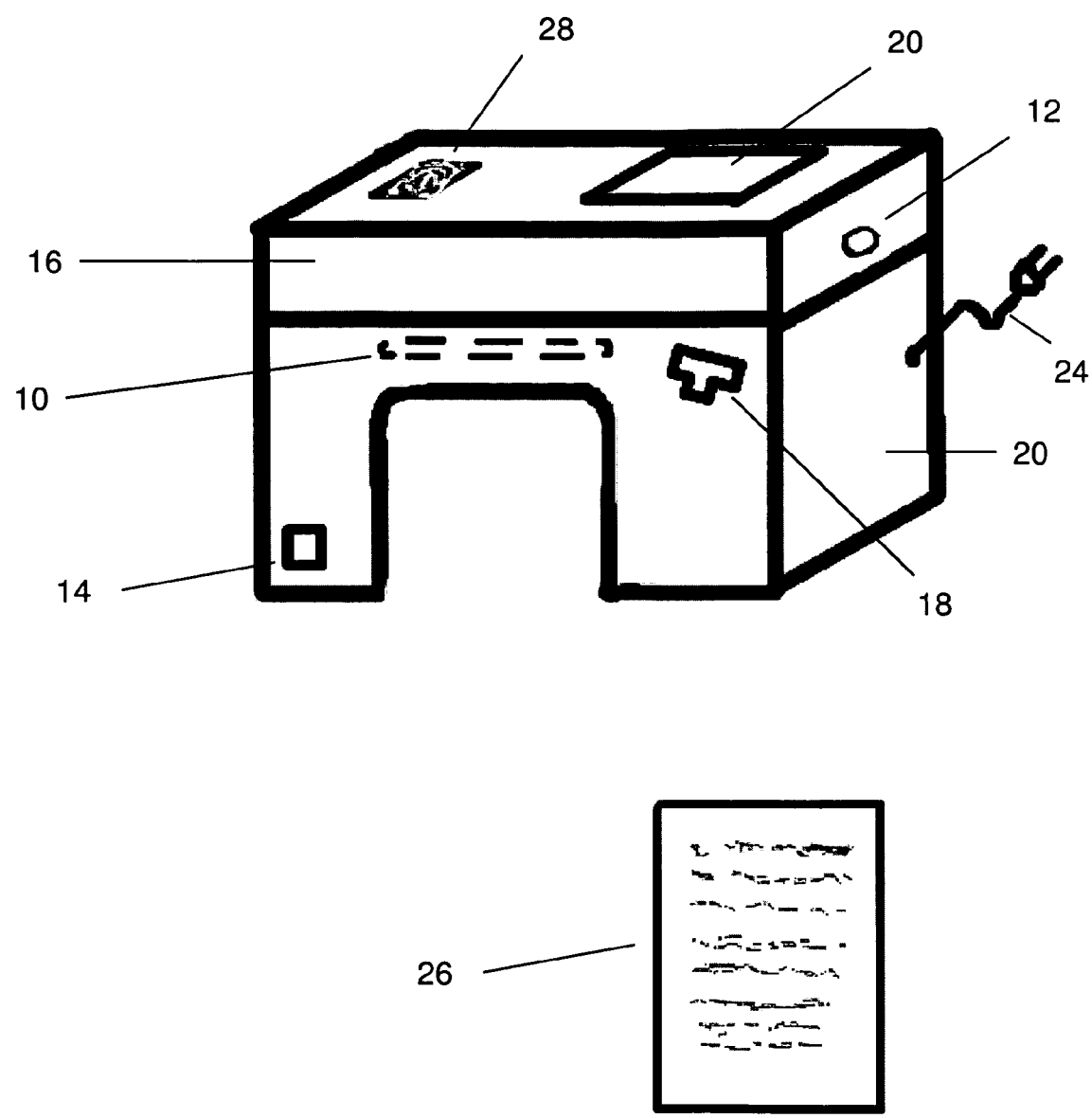
FIG. 11 is an environmental perspective of a Device to prevent and treat skin and nail infections

FIG. 11 illustrates a device to prevent and treat skin and nail infections.

Figure 12:
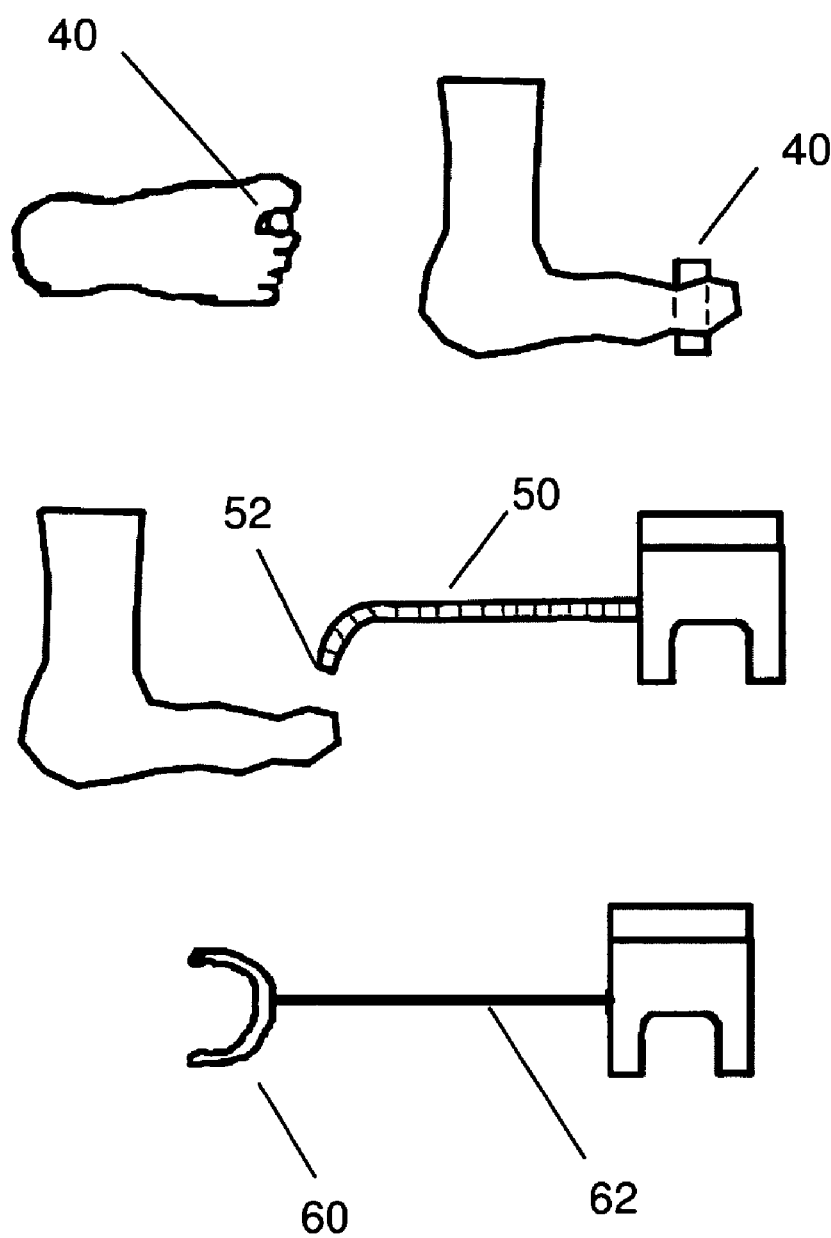
FIG. 12 is an environmental perspective of Special attachments to device to prevent skin and nail infections according to a further embodiment of the invention.

FIG. 12 illustrates special attachments for use with the treatment device.

Description of Invention

The method for the prevention and treatment of skin and nail infections combines the use of germicidal electromagnetic radiation with the previously unrecognized ability of said radiation to penetrate the nails and skin sufficiently to inactivate organisms.

The following descriptions of the presently contemplated best modes of practicing the invention is not to be taken in a limiting sense, but is made merely for the purpose of describing general principles of the invention. The scope of the invention should be determined with reference to the claims.

As noted above, the present invention employs germicidal radiation to prevent and treat skin and nail infections. To successfully treat these infections it is necessary to provide radiation that is germicidal in nature, is able to penetrate to the site of the infection, and is delivered for sufficient time and strength to inactivate the organism. Treatment is accomplished using the previously unrecognized ability of germicidal radiation to penetrate the skin and nails sufficiently to inactivate organisms that cause skin and nail infections by antigenosis or by geneticide. Also, although the description of the invention discusses human subjects, it is contemplated that the treatment can be used on both human and animal subjects.

Said method is capable of being used to treat and prevent all infections of the skin and nails. This includes the most common skin infections caused by *Staphylococcus aureus, Streptococcus pyrogenes, Psuedomonas aeriginosa*, and all other organisms that cause skin infections. It also includes nail infections caused by bacteria, fungi (including dermaphytes, yeasts, molds, and non-dermaphyte molds), viruses, and other microbes. Specifically, organisms causing fungal infections of the nails, said infection being termed onychomycosis, are included in the list of organisms treated by this invention.

UVC

The most recognized form of germicidal radiation is UVC radiation in the range of 240 to 280 nm. Radiation in this range is absorbed by the RNA and DNA of a cell and damages the ability of the cell to reproduce. Other forms of radiation have also been found to inactivate organisms including sources at 180 to 1370 nm and sources that emit in a high intensity pulsed manner. Although the applicant does not wish to be bound by any theory of operation it is believed that major effect of germicidal light is to damage an organism's genetic material so that it cannot reproduce or by damaging the cell so that it cannot survive and reproduce.

It has been observed that organisms vary in their resistance to the effects of germicidal radiation. For most organisms a dose of 5 to 10,000 mw-sec/cm$^2$ (5 mJ/cm$^2$ to 10 J/cm$^2$) is sufficient to completely inactivate an organism. This dose may be applied in several separate sessions, however, care must be taken that the organism does not recover and reinfest the area between treatments.

Preferentially, the radiation of choice is UVC is the range of 254 nm that can be readily produced by a low pressure mercury lamp or by a laser. This type of radiation source (generally a mercury lamp) is readily available from a number of manufacturers and there is an extensive list of inactivation doses for many organisms for this type of light. This type of radiation is the preferred form of radiation for disinfection of air in buildings such as hospitals and for disinfection of drinking water. A laser with output at approximately 254 nm is another preferred source of radiation. A laser could be more effective that a low pressure mercury lamp since it can precisely deliver a specified dose or radiation without affecting adjacent areas. This type of laser is currently commercially available and is used for manufacturing integrated circuits among other things. A medium pressure or high pressure mercury lamp are other preferred sources of germicidal radiation since they emit strongly in the UVC range while also containing other light ranges that are known to be germicidal such as UVB light. Xenon lamps also emit a significant portion of their light in the germicidal range and their non-germicidal component appears to work synergistically to reduce the amount of light needed to inactivate organisms.

It is possible to treat a nail or skin infection using radiation without knowing what organism causes the infection. However, doing so runs the risk of not applying sufficient radiation or conversely applying too much radiation. Therefore, when treating an infection it is best to make a diagnosis of what organism is causing the infection. Once the cause of the infection is determined, the practitioner can consult the UVC charts that are available from the manufacturers of UV germicidal lamps. Many charts list have more than 50 different types of organisms listed along with the dose of UV at 254 nm that is required to inactivate them. Charts are available from the American Ultraviolet Company (Murray Hill, N.J.), from the Atlantic Ultraviolet Corporation (Hauppauge, N.Y.), other manufacturers, and research organizations. The inactivation charts provided by American Ultraviolet Company and Atlantic Ultraviolet Corporation are incorporated by reference as if fully set forth herein.

Once the infection causing organism is determined and the necessary UV dose at 254 nm is obtained from a chart, a practitioner must determine the distance from the skin the lamp must be held and the amount of time the area should be irradiated to deliver the necessary dose. Manufacturers of germicidal lamps provide formulas to determine these parameters.

Example of Treating a Skin Infection

To treat a skin infection a practitioner would generally:
1. Determine the cause of the infection if possible
2. Determine the dose of germicidal radiation necessary to treat the infection taking into account the attenuation of the light as it penetrates
3. Determine how to apply the dose or doses of radiation
4. Apply the dose or doses of radiation
5. Follow-up after treatment to determine if the infection has been stopped
6. Provide additional treatment as necessary Step 1—Determine the cause of infection—To determine the cause of infection, a practitioner would either culture the organism from a sample or would make a clinical determination based on visual observations. If a definitive determination is not possible the practitioner would choose the most likely organism that requires a high inactivation dose in order to be sure that enough radiation was applied.

Step 2—Determine the dose of germicidal radiation— Next a practitioner would determine the dose of germicidal radiation necessary. Inactivation doses are available in charts for many of the organisms that cause skin infections such as *Staphylococcus aureus* (6,600 uw-sec/cm$^2$ to inactivate), *Streptococcus pyrogenes* (4,200 uw-sec/cm$^2$ to inactivate), and *Psuedomonas aeriginosa* (10,500 uw-sec/cm$^2$ to inactivate). Additionally, new organisms are being added all the time as more research is directed to the germicidal effects of UVC light. If an organism is not listed on the chart it may be possible to infer a probable inactivation dose. For example, of the more than 50 types of bacteria listed on one manufacturer's chart, all the inactivation doses ranged from 2,500 to 26,400 uw/cm$^2$ (with the exception of Anthrax spores which are especially difficult to treat and have a published range of 9,400 to 135,000 uw/cm$^2$ to inactivate). Therefore, if a person had a bacterial infection and it was not possible to determine its cause, a practitioner could irradiate the infection at the high end of the range to inactivate the infection. As germicidal treatment of infections becomes more common it is expected that the inactivation doses of all major organisms will be determined with greater accuracy and more definitive doses can be determined.

Skin infections are often difficult to treat due to encrustations and debris and due to the sensitivity of the area. While germicidal radiation is attenuated by encrustations and debris the radiation, if applied in the proper dose, enough should be able to penetrate sufficiently to have a beneficial effect. However, good practice would dictate that as much as possible all encrustations and debris be removed to maximize the benefits of the radiation. It may also be necessary to spread out treatments in particularly deep infections so that the surface of the infection may heal and permit easier application of radiation to the deeper levels (clear skin will permit radiation to pass more easily than thick and opaque encrustations. It may also be desirable to use a high powered tunable laser to provide precisely targeted UV to more recalcitrant infections.

The actual transmissivity of the light through the skin and the infection must also be taken into account to determine the proper dose. Since germicidal light is easily absorbed by the skin and any obstruction of caused by the infection, an assumed transmissivity rate of 1% is prudent unless the practitioner has more definitive information available. Thus if a practitioner determined that the infection was caused by *Staphylococcus aureus* (a common cause of skin infections) he could then consult a chart and determine the inactivation dose was 6,600 uw-sec/cm$^2$. Assuming a transmissivity rate of 1% and applying a factor of safety of 2 the practitioner would then need to apply 1,320,000 uw-sec/cm$^2$ to treat the infection.

Step 3—Determine how to apply the dose of radiation—If a practitioner determined that the infection was caused by *Staphylococcus aureus* and desired to apply a total dose of 1,320,000 uw-sec/cm$^2$ to treat the infection this could be achieved using a G6T5 low pressure lamp available from American Ultraviolet Company (AUC). The lamp uses fixtures and ballasts that are similar to fluorescent lights. The lamp provides 11 uw/cm$^2$ at a distance of one meter. If the lamp is held 6-inches from the infection the multiplication factor to convert the applied radiation 1-meter to the amount applied at 6-inches is obtained from a chart supplied by American Ultraviolet Company. This factor is 12. Therefore a G6T5 lamp held 6-inches from an infection will irradiate 132 uw/cm$^2$ (11 uw/cm$^2$ times the conversion factor of 12). Thus, a practitioner would need to irradiate a person for 10,000 seconds (1,320,000 uw-sec/cm$^2$ divided by 132 uw/cm$^2$) at a distance of 6-inches from the infection to inactivate an organism. Thus the total irradiation would be 167 minutes (10,000 seconds) and it may be desirable to apply the UVC in several doses in order to minimize the amount of UVC in each dose. This would also permit the first dose to kill the organisms closest to the surface and provide time to clean the infection of the dead organisms and retreat the infection. The depth of effective treatment would thus be greatly increased Step 4—Apply the radiation—Continuing with the example, the total dose of 167 minutes could be applied in three consecutive daily sessions of 56 minutes each and prior to each irradiation the infection could be cleaned to remove debris and any organisms that might have been destroyed by prior irradiations. A device similar to that shown in FIG. 11 may be used to administer the radiation.

Step 5—Follow-up after treatment—Once the radiation has been applied, the practitioner would schedule regular follow-up appointments to monitor the status of the infection. If the infection continued to spread, the practitioner would apply additional doses of radiation to inactivate the organism causing infection.

Step 6—Provide additional treatment as necessary—It is possible that the original treatment of the infection may not completely cure the infection due to a number of factors such as lower penetration of light than anticipated. If the infection has not totally cleared the practitioner would estimate the amount of clearing and apply additional treatments to provide complete eradication of the infection. For example, if only 50% of the infection had appeared to clear the practitioner may decide to apply 200% of the radiation originally applied to take into account that the remaining infection may be twice approximately twice as resistant as the half that was originally eradicated.

Treatment of Skin, Teeth, and Membranes of the Mouth

The same procedures used to treat skin could be used to treat the skin, teeth and membranes of the mouth although special care must be taken to prevent damage to these sensitive areas.

Germicidal light could be used to treat infections such as cold sores of the mouth caused by the Herpes virus.

Germicidal light could also be used on a periodic basis for by persons infected with the HIV or Aids virus to lower the virus counts in their saliva. This may have an overall positive effect on the health of the person and would also decrease the infectiousness of the saliva.

Germicidal light could also be used to prevent and treat dental caries. This would be especially effective once the teeth were cleaned of all plaque and the light could be easily delivered to the surface of the teeth and gums.

Special devices similar to those shown in FIG. 12 can be used to deliver light in the confined space of the oral cavity. One device would be an oral insert similar to a mouth guard that would form around the teeth. The insert could come in preformed sizes for a variety of mouth shapes or it could be specially formed for the person being treated. The insert would be made of a materially that is optically transparent to germicidal light such as fused quartz or Teflon and which could also diffuse the light evenly over the area being treated. The device could then be used to irradiate the inside of the mouth in a relatively uniform manner. Another special device could be used to deliver germicidal to a point in order to treat a specific cold sore or a specific cavity. The germicidal light could be delivered via a flexible wand which designed to transmit germicidal light.

Example of Treating a Nail Infection

Use of UVC (200 nm to 280 nm)

Treating a nail infection is similar to treating a skin infection with added attention to one item in particular. When treating a nail infection, special account must be taken of the transmissivity of the nail since its transmissivity is so low.

While it would be best to obtain a sample of the nail to be treated and determine its transmissivity it may be possible to extrapolate transmissivity from data collected on other nails.

For example, the transmissivity of UVC at 254 nm through nails was measured using an IL 1771 research grade radiometer. The data indicate that nails have a range of transmissivity for UVC at 254 nm of approximately 0.01% to 0.001%. In the absence of actual data it may be possible to approximate nail transmissivity as 0.05% to conservatively calculate the lowest theoretical effective dose.

Continuing the example, if it was determined that the nail could only transmit 0.05% of light at 254 nm and the organism required a dose of 9,000 uw-sec/cm$^2$ then at total of 2,000 times that amount of energy, or 18,000,000 uw-sec/cm$^2$ (18 Joules/cm$^2$) would need to be applied to inactivate the organism. A factor of safety would also need to be applied similar to that for skin infections. Therefore, a dose of approximately 36 Joules/cm$^2$ would be appropriate if a factor of safety of two was applied.

Use of UVB (280 nm to 315 nm)

It is important that the transmissivity for the wavelength of treatment be taken into account. For example, if nail treatment were to involve the use of UVB light at 313 nm, it would be necessary to determine or estimate the transmissivity of light at that wavelength specifically. Light penetration for this wavelength of light may be estimated from FIG. 3 to be approximately 10 times greater than light at 254 nm. Therefore, in the absence of actual nail transmittance data it may be estimated to be approximately 0.5% or ten times the value used for UVC 254 nm light.

The relative germicidal efficiency of UVB must also be taken into account along with transmissivity. Light at 313 nm has approximately $\frac{1}{1000}$ the germicidal effectiveness of light at 254 nm.

Therefore, although ten times more light may penetrate the nail, the dose would still have to be increased 100 fold (1000 divided by 10) to achieve approximately the same germicidal ability. For example, if it was determined that the nail could only transmit 0.05 percent of light at 254 nm and the organism required a dose of 9,000 uw-sec/cm$^2$ to inactivate, a total of 200,000 times that amount of energy, or 1,800,000,000 uw-sec/cm$^2$ (1,800 Joules/cm$^2$) would need to be applied to inactivate the organism. This dose would probably be impracticable to apply without thermal injury to the patient and illustrates why UVB is not generally considered germicidal in and of itself.

It should be noted that while UVB at 313 nm is not particularly germicidal, light in the lower UVB range, say around 280 to 290 nm is almost as germicidal as some UVC light. Thus light in the lower part of the UVB range could be used by itself to successfully treat skin and nail infections.

Use of UVA (315 nm to 400 nm)

Use of UVA light to inactivate organisms is also possible; however, it has a much less potent germicidal effect. For example, UVA light at 340 nm has approximately the same germicidal strength as UVB light at 313 nm but it should be able to penetrate the nail better. Thus it may be possible to use a lower dose of UVA at 340 nm than UVB at 3133 nm. However, even if the dose was decreased by half it would still be too high to apply to the nails without generating significant side effects such as a major sun burn. Thus while UVA light may be used in conjunction with other germicidal light it is not an ideal source by itself.

While UVA (315 nm to 400 nm) is not normally considered germicidal by itself it is possible to modify the environment to enhance UVA's ability to act germicidally on organisms causing skin and nail infections. Modifications that enhance UVA's germicidal capabilities include the addition of a high ionic strength solution (such as saline), increasing the pH, and increasing the oxygen content (by adding peroxide or other high oxygen content solution or by directly applying a small amount liquid oxygen to a infected area). The mechanism of organism destruction is different than that of germicidal light in the UVC or UVB range since UVA in the modified environment acts to disrupt cell membranes instead of damaging its genetic material. Modifying the environment in this manner thus permits the use of UVA light to treat skin and nail infections.

Use of Medium Pressure Mercury Lamp

Light generated from a medium pressure mercury lamp has an abundance of germicidal light in the UVC and UVB range. This type of light is beginning to be more commonly used to disinfect drinking water and wastewater and its characteristics is the subject of greater study. The variety of germicidal wavelengths present may also work synergistically together thus requiring a lower overall dose to successfully treat a nail infection. Also, the spread of the wavelengths of light through the nail may also reduce any heat that might be generated by the treatment. To use this type of light successfully it is necessary to estimate the overall dose to inactivate an organism as well as the wavelength-weighted transmissivity of the nail to this broad band light source.

Use of Other Types of Germicidal Light

The description of the invention focuses UVC light to prevent and treat infections. However, any electromagnetic radiation that has antimicrobial effects is also contemplated by this method to treat infections.

Germicidal light combining a continuum of germicidal wavelengths and other wavelengths generally considered non-germicidal is another possible treatment method for nail infections. Varying the mode of application (i.e. pulsing, etc.) may also increase the efficacy of such light. Specifically, light generated from a Xenon lamp has an abundance of germicidal light in the UVC and UVB range as well as light in other bands that seem to work synergistically together thus requiring a lower overall dose to successfully inactivate an organism. This type of light is beginning to be used in water and wastewater treatment. It is also being used in food processing. It has the potential to be more effective than even pure germicidal light in the UVC range since its synergistic effect often can inactivate an organism at a significantly lower dose. Another advantage with respect to the treatment of nails is that this type of light employs a variety of wavelengths of light and the longer wavelengths can penetrate the nails much more easily than UVC. While the longer wavelengths of light are not considered germicidal by themselves they can act synergistically with germicidal light to inactivate an organism. Thus this type of light can be used particularly effectively to treat skin and nail infections due to its greater ability to penetrate.

An example of electromagnetic radiation other than UVC that can be used to inactivate organisms is broad spectrum, high intensity, pulsed light. Page 5 of *Kinetics of Microbial Inactivation for Alternative Food Processing Technologies* (U.S. Food and Drug Administration Center for Food Safety and Applied Nutrition, Jun. 2, 2000) notes that a single pulse of such light (with a wavelength of 170 to 2600 nm) with an intensity as small as 1.25 J/cm$^2$ is sufficient to inactivate *Staphylococcus aureus*. This is significantly less that the 6.6 J/cm$^2$ of UV at 254 nm required and makes the use of this type of radiation particularly attractive. This type of light may also penetrate more easily (longer wavelength light penetrates more easily than short wavelength light) and is better tolerated than UVC which is also advantageous. This type of light is an excellent example of how other wavelengths of light can be synergistically combined with UVC germicidal light to enhance treatment of infections.

PurePulse Technologies, Inc. sells a pulse light that can deliver this type of radiation under the trademark PUREBRIGHT™. This type of light generally has a DC power supply which charges capacitors, a switch which controls the discharge of the capacitors, a trigger circuit which permits the capacitors to be discharge at preprogrammed time intervals, a manual discharge mode, and one to four flash lamps mounted in reflectors to direct the light emitted from the lamps. This configuration could be modified and refined to be more suitable for use treating skin and nail infections. The method to use this device would be similar to that described above for using a low-pressure mercury lamp that is described above. Research is currently being conducted on a wide range of organisms to determine the energy necessary to inactivate each organism and what is the best way to apply such energy (i.e. one large pulse or a number of smaller pulses).

The effectiveness of multi-spectrum germicidal light for inactivation of organisms at lower overall doses than UVC alone indicates that other parts of the spectrum have germicidal properties. The exact inactivation mechanism is not known, however, it probably is a combination of several mechanisms that act together to render the cell inactivated or incapable of reproducing. Although the author does not wish to be bound as to the mechanism of inactivation used, several observations may be made. In addition to probable damage to the organism's genetic material, the multi-spectrum light could damage other components of the organism necessary to its vital functions. It may also provide instantaneous heating of small areas in the cell which would not kill the organism by high heat but which are nonetheless effective in damaging the cell wall and inactivating the organism.

It is likely that there are certain types of radiation that are more effective than others at inactivating organisms or preventing them from reproducing. These types of radiation are likely contained in the range of pulsed light (170 to 2600 nm) but other parts of the spectrum may also be germicidal. Therefore, the proposed method to prevent and treat skin and nail infections encompasses any forms of electromagnetic radiation that can be used germicidally to inactivate an organism or prevent it from reproducing.

Prevention of Skin and Nail Infections

Additionally, microbial infections can be prevented by the periodic application of electromagnetic radiation to prevent incipient infections from occurring. This would be particularly desirable in populations prone to fungal infections (such as diabetics and the elderly) and those who require constant monitoring (such as those in hospitals and nursing homes). It would also be very desirable for those whose health could be significantly threatened by a fungal infection (such as diabetics or immunocompromised individuals). Fungal infections of the nails in a diabetic person can progress and associated complications can lead to amputation of a finger or toe. The dose necessary to prevent fungal infections would be significantly less than that necessary to eradicate a full blown infection. The dose would be approximately in the range of half of the standard dose and should be sufficient to inactivate approximately 99% of the organisms that may be present. This dose would be applied on a periodic basis (daily, weekly, monthly, or quarterly depending on the estimated risk of infection and the dose applied) to help keep a person infection free.

FIG. 9 is an illustration of germicidal light being used to prevent a nail infection such as onychomycosis.

FIG. 10 is an illustration of germicidal light being used to prevent a skin infection such as athletes foot.

FIG. 11 is an illustration of a device that can be used to prevent skin and nail infections. FIG. 12 is an illustration of special attachments that may be used with the device to treat skin and nail infections.

The foregoing is illustrative of the present invention and is not to be construed to be limiting thereof. Although a few exemplary embodiments of this invention have been described, those skilled in the art will readily appreciate that many modifications are possible in the exemplary embodiments without materially departing from the novel teachings and advantages of this invention.

Enhancement of Treatment

There are a number of ways that treatment by germicidal radiation may be enhanced. These enhancements are discussed further in this section Creation of an Unfavorable Environment It has been shown that organisms are less resistant to germicidal radiation of they are subject to environmental stresses. Creation of an unfavorable environment is therefore one way to enhance treatment with germicidal radiation. Deprivation of food and nutrients, unfavorable temperature regimes, varying of pH, etc. are all techniques that may be used to enhance the effectiveness of treatment using germicidal light. Thus the invention may be supplemented by the creation of unfavorable environmental conditions for the organisms.

These enhancements are therefore included as part of this invention.

Change of Skin or Nail Characteristics

Germicidal light has very low penetration power. Therefore, any modification of skin or nail characteristics to enhance penetration would have a significant beneficial effect on treatment effectiveness. For skin this may include the application of preparations that change the characteristics of the epidermis to permit greater penetration of germicidal penetration. It may also include the treatment of any skin abnormalities such as calluses or scabs to remove obstacles to penetration by germicidal light. For nails this would include compounds that may enhance the transmission of light through the nails. It would also include partial or total removal of the nail (perhaps through the application of urea or a similar compound) to permit better penetration of the germicidal light to the site of the infection.

These enhancements are therefore included as part of this invention

Enhancement via Use of Media to Transmit Light

The application of germicidal radiation could be enhanced by the use of a media to transmit the light effectively. The media may be a special gas, liquid, or solid which can maximize the application of light to the affected area or prevent it from being applied in undesirable areas. A form of application could be a gel applied to the infected area which permit the light unit to be place in contact with the gel or perhaps just focused on the gel.

These enhancements are therefore included as part of this invention.

Use of Antibiotics

Topical antibiotics have been shown to have only a minimal effect. For example Penlac, the leading topically applied antibiotic, has less than a 12% total cure rate when applied daily basis for more than 8 months. However, topical antibiotics can be used to enhance treatment using germicidal lights. Similarly, topical antibiotics could be used synergistically with germicidal light to treat skin infections.

Systemic antibiotics also have limited effect on nail infections. For example, LAMISIL™, the leading systemic antibiotic for nail infections has only a 40% total cure rate for nail infections. However, systemic antibiotics could be used synergistically with germicidal light to greatly enhance their effectiveness.

These enhancements are therefore included as part of this invention.

Use of Other Light Spectrums Acting Synergistically

While the UVC, and UVB to a lesser extent, range of light is the most potent germicidally, other parts of the light spectrum may be used to further enhance the effectiveness of treatment. It is well known that multiple stresses on an organism are more likely to damage it. Thus, other parts of the light spectrum may be used to create added stress on the organisms and cause them to be inactivated successfully using lower doses of germicidal light. For example, longer wavelengths of light generate heat which although it may not be sufficient to kill an organism by itself could be used in conjunction with germicidal light to successfully treat an infection.

This synergistic action can be seen in the use of Xenon and other broad spectrum lamps that have been used to disinfect air and water. The synergistic action of the light spectrums greatly enhances the germicidal ability of light.

These enhancements are therefore included as part of this invention.

Use of Lasers

Lasers have a number of characteristics that make them particularly useful in treating skin and nail infections using germicidal light.

First, some lasers (e.g. tunable lasers) have the ability to be tuned to a very precise point of the light spectrum thus permitting the most effective wavelength to be applied to an infected area.

Second, it is possible to tightly focus a laser and thus precisely apply energy where needed. This permits treatment of the infected area only without involving any non infected area. For example, it is possible to treat nail infections without affecting the surrounding skin at all. Also, it is possible to tailor the amount of energy applied to different parts of an infection. It is thus possible to map an infection precisely and determine if more germicidal radiation should be applied in some areas of the infection.

Third, lasers tend to have higher power output than other types of light sources making the application of high energy levels extremely efficient.

Lasers also can be pulsed which may assist in their ability to penetrate more deeply. It may also be possible that the coherent nature of the light in a laser may permit it to penetrate more deeply in certain mediums.

Within the range of 240 nm to 280 nm, it appears that the primary mechanism is due to deformation of the organisms DNA. Literature indicates that light in the range of 257 to 260 nm may be most effective for most organisms; however, different organisms have shown various sensitivities to different parts of the UVC spectral region. There are several tunable lasers on the market at the present time that could be used to treat infections with this specific wavelength (such as the PAL laser manufactured by Light Age, Inc.).

Excimer lasers are also possible devices that can be used. Argon Fluoride at 193 nm, Krypton Fluoride at 248 nm, and Xenon Chloride at 308 nm have all been shown to have some germicidal ability. However, of the excimer laser Krypton Fluoride at 248 nm has been show to be most germicidal, followed by Argon Fluoride at 193 nm, and lastly Xenon Chloride at 308 nm. GAM lasers manufactures different types of excimer lasers which may be suitable for these applications. Also, a frequency tripled Ti:sapphire laser could be used since it deliver energy at 254 nm or 280 nm. The foregoing list is intended to be illustrative and not a comprehensive list of lasers that could be used.

Lasers can be used to generate significantly higher dosages than may be easily generated by other forms of light. If extremely high dosages of light are used it may be desirable to cool the skin by use of water or by spraying a cryogen to cool the skin. Use of cooling would be much more effective than when used for other longer wavelengths of light since much less heat is generated in the first place and all such heat will be on the surface of the skin while longer wavelength light heats the lower layers of skin.

These enhancements are therefore included as part of this invention.

Description of Device to Prevent and Treat Skin and Nail Infections

The treatment device may have any combination of the following components:

Light Source (10) that can be tuned to a specified spectral output or a fixed spectral output.

A timer (12)

A means (14) to determine the intensity of the light

A processing unit (16) that can perform calculations, store data, track usage, troubleshoot problems, etc.

A camera (18) to take pictures

A shield (20) to prevent light from illuminating other areas
Safety Labels (22)
Ground fault protector (24)
Safe Operating Instructions (26)
Security devices (28)
A connection (30) for special attachments FIG. 12 illustrates some of the special attachments that could be used for treatment and includes the following:

- An attachment (40) that can provide light to hard to reach areas such as those between the toes.
- An attachment that transmits light via a flexible cable (50) and delivers this light at the end of the cable (52) to treat a specific area.
- An attachment that can be inserted in the mouth (60) and can receive light from a flexible cable (62) that can transmit such light.

Preferably, a treatment device is provided to prevent and treat skin and nail infections incorporating the light source, and which can incorporate a number of special features to enhance treatment and promote safety. Such a treatment device is shown in FIG. 11.

For example the treatment device may contain a light source (10) that can be tuned to a specific spectral output or has a fixed spectral output. This can be accomplished by the use of a tunable laser, multiple lamps, or by the use of one or more filters to screen out wavelengths that are not desirable. The treatment device may also contain very small lamps capable of being inserted in small spaces or directly on the surface to be treated.

Preferably, the treatment device can have a timer (12) and a means (14) to determine the intensity of the light being provided such as a spectrometer or radiometer. The device can also have a processing unit (16) that can take the time of radiation and the intensity and determine the dosage of light applied. The device can also be programmed to take into account the transmissivity of the nails being treated, if it were being used to treat nails. The user of the device can then input the desired dosage of light to be applied and the device can then accurately deliver it.

The treatment device can also have a number of additional features which can be used separately or in various combinations that make it easy to track the use of the device. The device can use the processing unit (16) to retain a memory of each usage session including how long the session was, the intensity of light supplied, and the overall dosage applied during the session. It would preferably have means for the operator to add an identifier of the patient being treated for future therapy use. The device may also be equipped with a camera (18) to take photos of the treated area. These photos could be stored with other treatment parameters making it easy to track the course of treatment over several sessions. The device may also accept a set of treatment sessions and monitor the records and provide reminders of when the next treatments should be undertaken.

The processing unit (16) of device may be equipped with a computer which will permit diagnostic activities on the correct functioning of the device such as monitoring the lamp output to ensure it does not degrade below a certain specified output. The computer can also interface with the Internet via a wired or wireless connection and transmit all information to a remote source. The connection can also be used by a technician to troubleshoot the device remotely and determine the cause of any problems.

The device to prevent and treat skin and nails infections can also be equipped with a number of attachments that can be used to apply germicidal light in hard to reach or sensitive areas. Some of these attachments are illustrated in FIG. 12. For example, there could be an attachment (40) that could be inserted between toes to irradiate the area between toes that is especially vulnerable to athlete feet infections. Another attachment (50) could be used to apply light to a small area of the nail or skin by use of a flexible wand that can transmit germicidal light to the end of the wand (52). This could also be used to irradiate the area between the toes. This type of wand could also be used to apply light to a specific area of the mouth. Another special attachment (60) can be an insert that fits around the teeth in the mouth similar to a mouth guard used by athletes to prevent injuries or by persons who grind their teeth at night. This type of attachment (60) can be made of an optically transparent material and a material to diffuse light to permit the germicidal light to be applied uniformly inside the mouth. Light for the attachment (60) can be supplied from the germicidal unit by use of a fiber optic cable (62) or other similar means.

The device to prevent and treat skin and nail infections can contain a number of safety features. For example the special attachments (FIG. 12) to irradiate the area between toes could be coated with a material such as Teflon which is easy to clean and which would protect the person if the encase lamp was broken. Another safety feature would be another type of attachment to treat the areas between the toes that used a flexible wand to transmit the light thus eliminated the need for a small lamp that can fit between the toes.

Other safety features include the use of a shield to prevent the light from illuminating other areas (20), safety labels (22), a ground fault protector (24) in case of a short circuit, and an optically transparent barrier to prevent accidental damage to the lamp. A specific safety feature claimed is the instructions for safe use of the device to be included with each device (26).

The device can also incorporate security devices (28) to prevent unauthorized use. This can include a fingerprint reader, password protection, or remote enablement where a person makes a call to receive a valid operational code to permit the equipment's use.

The device can also have a connection (30) for special attachments so that light can be routed and supplied to these attachments. One skilled in the art would recognize that although these treatment device features have been describe in alternative language, that the features can be used together, individually or in any combination of features.

DESCRIPTION OF FURTHER PREFERRED EMBODIMENTS

Several of the preferred embodiments make use of light as a specific composition of matter composed of photons at specific wavelengths that interact with the biomolecules present in genetic material of a cell. This specific composition of matter causes the genetic material of the cell to be damaged and prevents the cell from reproducing. This specific composition of matter can also be used to overwhelm the cellular processes mediated by genetic material thus killing the organism directly.

Further Embodiment

In a further preferred embodiment, the radiation is that which is necessary to inactivate the organisms that cause infections of the skin and nails. The radiation is a specific composition of matter composed of photons at specific wavelengths that interact with the biomolecules present in genetic material of a cell. This specific composition of matter causes the genetic material of the cell to be damaged and prevents the cell from reproducing. In the preferred embodiment the organism may be inactivated by disabling its ability to reproduce or it may destroy the organism by overwhelming the genetic processes of the cell thus causing its death directly.

In a preferred embodiment of the invention the organisms inactivated are those that cause infections of the skin and nails. These organisms include bacteria, fungi (including dermaphytes, yeasts, molds, and non-dermaphyte molds), viruses, and other microbes. Specifically, organisms causing fungal infections of the nails, said infection being termed onychomycosis, are included in the list of organisms treated by this invention.

In a preferred embodiment, it may be necessary to irradiate the skin and nails for several times in order to completely inactivate the organisms in order to prevent and treat skin and nail infections. The electromagnetic radiation in the preferred embodiment consists of radiation in the UVC range (100 to 280 nm and more specifically in the range of 240 to 280 nm) that is capable of rapidly inactivating an organism. In a preferred embodiment, the UVC source may be a low, medium, or high pressure mercury vapor lamp or a laser.

In a preferred embodiment, the amount of irradiation received during one treatment will be in the approximate range of 5 mJ/cm$^2$ to 100 J/cm$^2$. In a preferred embodiment it may be desirable to apply the radiation in several sessions.

Another preferred embodiment of the method to prevent and treat infections of the skin and nails involves irradiating the infected area using a medium pressure or high pressure mercury lamp which contains a variety of germicidal bands of lights. In a preferred embodiment, the amount of irradiation received during one treatment will in the approximate range of 5 mJ/cm$^2$ to 100 J/cm$^2$. In a preferred embodiment it may be desirable to apply the radiation in several sessions.

Another preferred embodiment of the method to prevent and treat infections of the skin and nails involves irradiating the infected area using a lamp capable of generating light in the UVB range between 280 and 315 nm. In a preferred embodiment, the amount of irradiation received during one treatment will in the approximate range of 50 mJ/cm$^2$ to 100 J/cm$^2$. In a preferred embodiment it may be desirable to apply the radiation in several sessions.

Another preferred embodiment of the method to prevent and treat infections of the skin and nails involves irradiating the infected area using a lamp capable of generating light in the UVA range between 315 and 400 nm. In a preferred embodiment, the amount of irradiation received during one treatment will in the approximate range of 50 mJ/cm$^2$ to 100 J/cm$^2$. In a preferred embodiment it may be desirable to apply the radiation in several sessions. In the preferred embodiment it may be desirable to modify the environment of the infection to enhance UVA's germicidal capabilities include the addition of a high ionic strength solution (such as saline), increasing the pH, and increasing the oxygen content (by adding peroxide or other high oxygen content solution or by directly applying a small amount liquid oxygen to a infected area or by otherwise increasing the oxygen content).

In an additional preferred embodiment the electromagnetic radiation used may be from a polychromatic pulsed source such as those used to disinfect food and instruments. In additional preferred embodiments any electromagnetic radiation can be used which is capable of inactivating the infection causing organisms, is able to penetrate sufficiently, and is safe for exposure to humans and animals in the doses contemplated. In a preferred embodiment, the amount of irradiation received during one treatment will in the approximate range of 5 mJ/cm$^2$ to 500 J/cm$^2$. In a preferred embodiment it may be desirable to apply the radiation in several sessions.

A preferred embodiment of a device to prevent and treat skin and nail infections incorporates features to enhance treatment and promote safety. The preferred device may have the power needed to provide between 1 mJ/cm2 to 1000 J/cm2 or any range of power therein.

The device may have the ability to provide light in a wide range of wavelengths and it may have the ability to filter out undesirable wavelengths. The device may contain a light source that can be tuned to a specific spectral output accomplished by the use of a tunable laser, multiple lamps, or by the use of one or more filters to screen out wavelengths that are not desirable. The treatment device may also contain very small lamps capable of being inserted in small spaces or directly on the surface to be treated.

The preferred treatment device can have a timer and a meter to determine the intensity of the light being provided. The device can also have a processing unit that can take the time of radiation and the intensity and determine the dosage of light applied. The device can also be programmed to take into account the transmissivity of the nails if it were being used to treat nails.

The treatment device can also have a number of features that make it easy to track the use of the device. The device can have a memory of each usage session including how long the session was, the intensity of light supplied, and the overall dosage applied during the session. The device can also be equipped with a camera to take high resolution photos of the treated area. These photos could be stored with other treatment parameters making it easy to track the course of treatment over several sessions. The device can also accept a set of treatment sessions and monitor the records and provide reminders of when the next treatments should be undertaken.

The device can be equipped with (or adapted to communicate with) a computer or remote device which will permit diagnostic activities on the correct functioning of the device such as monitoring the lamp output to ensure it does not degrade below a certain specified output. The computer can also interface with the Internet via a wired or wireless connection and transmit all information to a remote source. The connection can also be used by a technician to troubleshoot the device remotely and determine the cause of any problems.

The device to prevent and treat skin and nails infections can also be equipped with a number of attachments that can be used to apply germicidal light to hard to reach or sensitive areas. For example, there could be an attachment that could be inserted between toes to irradiate the area between toes that is especially vulnerable to athlete feet infections. Another attachment could be used to apply light to a small area of the nail or skin by use of a flexible wand that can transmit germicidal light to the end of the wand. This could also be used to irradiate the area between the toes. This type of wand could also be used to apply light to a specific area of the mouth. Another special attachment can be an insert that fits around the teeth in the mouth similar to a mouth guard used by athletes to prevent injuries or by persons who grind their teeth at night. This type of attachment can be made of an optically transparent material and a material to diffuse light to permit the germicidal light to be applied uniformly inside the mouth.

The device to prevent and treat skin and nail infections can contain a number of safety features. For example the special attachments to irradiate the area between toes could be coated with a material such as Teflon which is easy to clean and which would protect the person if the encased lamp were broken. Another safety feature would be another type of attachment to treat the areas between the toes that used a flexible wand to transmit the light thus eliminated the need for a small lamp that can fit between the toes.

Other safety features include the use of a shield to prevent the light from illuminating other areas, safety labels, ground fault protectors in case of a short circuit, and an optically transparent barrier to prevent accidental damage to the lamp. A specific safety feature claimed is the instructions for safe use of the device to be included with each device.

The device can also incorporate security devices to prevent unauthorized use. This can include a fingerprint reader, password protection, or remote enablement where a person makes a call to receive a valid operational code to permit the equipment's use.

The preferred embodiment of the treatment device may contain any combination of the aforementioned features.

Other Preferred Embodiments

For particularly difficult infections, it is beneficial to combine the said method of treatment with adjunct therapy including the application of oral and topical medications. This combination will work synergistically to effect a cure in a shorter period of time, in a more complete manner, or in a manner that creates less probability of relapse. Accordingly, a preferred embodiment is to combine the said method of treatment with adjunct therapy including the application of oral and topical medications as deemed appropriate by those skilled in the field.

Use of UVA (315 nm to 400 nm) may also be employed to inactivate organisms, particularly if the light is used in conjunction with other types of germicidal light or the environment modified to enhance the germicidal potency of UVA.

Use of additional wavelengths of light (similar to those generated by a Xenon lamp) may also be used to synergistically enhance the effect of germicidal irradiation. This is another preferred embodiment.

It is well known that certain organisms can repair genetic damage if they have access to certain wavelengths of light. This is known as photoreactivation repair of genetic damage. Accordingly, another preferred embodiment of the invention is to control the environment of the skin or nail after treatment such that light is not present thus preventing genetic damage from being repaired.

While some organisms use light to repair genetic damage, other organisms are better able to repair genetic damage only if no light is present. This is known as dark mediated repair of genetic damage. Accordingly, another preferred embodiment of the invention is to control the environment of the skin or nail after treatment such that no light is present thus preventing genetic damage from being repaired.

Other preferred embodiments of the invention rely on creating a hostile environment that make the survival of the organism more difficult to survive and thus work synergistically with the germicidal radiation to kill the organism. For example, most organisms causing fungal nail infections are aerobic. Thus, if the source of oxygen was limited after treatment it would enhance the inactivation dose of germicidal light. This could be accomplished by application of a thick ointment (such as petroleum jelly) or encasement of the nail in a membrane in which a relatively inert gas (such as nitrogen) was present thus preventing oxygen from reaching the organism.

Other preferred embodiments include means to enhance the penetration of germicidal light. One such method would be the application of urea to a nail to dissolve most of the nail and thus expose the nail bed to direct radiation from the germicidal light.

Other preferred embodiments include using germicidal light to treat animals that have skin, nail, claw, or hair infections. The germicidal light may also be applied to prevent such infections also.

Other preferred embodiments may include dosages of 5 mJ/cm$^2$ to 500 J/cm$^2$ if the radiation is of a wavelength that it can be applied safely in higher doses (this would be most applicable if multi-spectrum light is used). The light may be of multiple wavelengths and may be coherent or incoherent, and may be pulsed.

Further Alternative Embodiments

The electromagnetic radiation in an alternative embodiment may be from UVA radiation (315 to 400 nm).

The electromagnetic radiation in an alternative embodiment may also be from the visible part of the spectrum.

The electromagnetic radiation in an alternative embodiment may be from infrared radiation.

The electromagnetic radiation in an alternative embodiment may be from radiation from a combination of visible and non-visible parts of the light spectrum.

The electromagnetic radiation in an alternative embodiment may be from a pulsed source including a xenon pulse source or a laser.

The electromagnetic radiation in an alternative embodiment may be incoherent or coherent such as a laser.

The electromagnetic radiation in an alternative embodiment may be single spectrum or multi-spectrum.

In an alternate embodiment, the amount of irradiation received during one treatment may be substantially more or less than the 5 to 10,000 mw-sec/cm$^2$ of the preferred embodiment. In all circumstances the total amount of irradiation shall be within the limits deemed safe by the medical community for treatment of a disease or infection.

Accordingly, this invention can be used to prevent and treat a wide variety of skin and nail infections. It has the following advantages over the current method of treatments for these infections:

- With respect to treatment using oral medications, the invention eliminates unwanted and potentially dangerous side effects (such as liver problems) that such medications can cause.
- With respect to treatment using oral medications, the invention uses a very small number of treatments (one to perhaps a dozen) to eliminate the infection while medications must be taken continuously for several months.
- With respect to treatment using oral medications, the proposed treatment has the potential to be significantly less expensive than the current cost of $600 to $1200 for medicine.
- With respect to treatment using oral medications, the infection can be eliminated in much less time since the course of treatment would vary from approximately one day to one month whereas the medications must be taken from three to six months.
- With respect to treatment by inducing a pigment and using a high energy light to destroy an infection by excessive heat, the invention eliminates the need to separately induce a pigment in the organism before treatment begins. This saves time, cost, and eliminates the chance of side effects resulting from inducing the pigment.

With respect to treatment by inducing a pigment and using a high energy light to destroy an infection by excessive heat, the invention eliminates the need for a large amount of energy to destroy the organisms by excessive heat which may also cause damage and discomfort to the patient. The invention uses significantly less energy and thus has a much lower risk of complications.

With respect to other treatments used for existing infections, this treatment can also be used periodically to prevent infections from becoming established. This is particularly desirable for those who are predisposed to skin and nail infections or persons that such infections pose a significant threat.

Although the descriptions above contain many specificities, these should not be construed as limiting the scope of the invention but merely as providing illustrations of some of the presently preferred embodiments of this invention. For example, other sources of radiation may be used if they have the properties necessary to inactivate organisms, penetrate sufficiently, and are safe to humans or animals, etc.

Thus the scope of this invention should be determined by the appended claims and their legal equivalents, rather than by the examples given.

I claim:

1. A method of treating a microbial infection in a patient, comprising:
   evaluating the infection;
   calculating an amount of energy required to inactivate microbes in the infection;
   calculating an amount of the light of about 100 nm to 400 nm that is required to achieve the amount of energy, wherein calculating includes taking into account at least depth of area with the infection through which the light must be transmitted; and
   administering the amount of light to the infection, wherein the intensity of the light at least substantially inactivates microbes in the infection and wherein no light absorbing substance is added to the microbes.

2. The method of claim 1, wherein the light is absorbed directly by genetic material of the microbes, the genetic material being at least one of RNA and DNA.

3. The method of claim 2, wherein the light absorption causes dimerization of at least some pyrimidine molecules of the at least one of the RNA and DNA.

4. The method of claim 1, wherein administering light to the infection does not cause severe erythema of area surrounding the infection.

5. The method of claim 1, wherein administering light to the infection does not substantially raise the temperature of area surrounding the infection.

6. The method of claim 1, where administering light to the infection includes administering light to multiple locations in a single application.

7. The method of claim 1, wherein administering light to the infection includes administering light in multiple discrete applications.

8. The method of claim 7, wherein administering light in multiple discrete applications includes administering an amount of radiation of about 5 to 10,000 mj/cm$^2$ during each of the discrete applications.

9. The method of claim 7, wherein administering light in multiple discrete applications includes administering an amount of radiation of about 5 mj/cm$^2$ to 100 j/cm$^2$ during each of the discrete applications.

10. The method of claim 1, wherein administering light to the infection includes administering light with a xenon light source.

11. The method of claim 1, wherein administering light to the infection includes administering a multispectrum light having a substantial portion of the administered light of about 100 nm to 400 nm.

12. The method of claim 1, wherein administering light to the infection includes administering a multispectrum light having a substantial portion of administered light of about 170 nm to 2600 nm.

13. The method of claim 1, wherein administering light to the infection includes administering a pulsed polychromatic light having a substantial portion of the administered light of about 100 nm to 400 nm.

14. The method of claim 1, wherein administering light to the infection includes administering a broad spectrum pulse light source and administering at least 1.25 J/cm$^2$ of energy to the infection.

15. The method of claim 1, wherein administering light to the infection includes administering light of about 240 nm to 280 nm.

16. The method of claim 1, wherein administering light to the infection includes administering light of about 240 nm to 315 nm.

17. The method of claim 1, wherein administering light to the infection consists of administering light at a range and amount that is insufficient to kill all of the microbes.

18. The method of claim 1, wherein administering light to the infection includes administering light outside of the ultraviolet range to enhance treatment of the infection.

19. The method of claim 1, wherein the infection is in a nail of the patient.

20. The method of claim 1, wherein the patient is an animal.

21. The method of claim 1, further comprising, administering light to area with the infection prior to detecting visible signs of the infection.

22. A method of treating a microbial infection in a patient, comprising:
    evaluating the infection;
    calculating an amount of the light of about 100 nm to 400 nm that is required to achieve at least 1.25 J/cm2 amount of energy, wherein calculating includes taking into account at least depth of area with the infection through which the light must be transmitted; and
    administering the amount of light to the infection, wherein the intensity of the light at least substantially inactivates microbes in the infection and wherein no light absorbing substance is added to the microbes.

23. The method of claim 22, where administering light to the infection includes administering light to multiple locations in a single application.

24. The method of claim 22, wherein administering light to the infection includes administering light in multiple discrete applications.

25. The method of claim 24, wherein administering light in multiple discrete applications includes administering an amount of radiation of about 5 to 10,000 mj/cm$^2$ during each of the discrete applications.

26. The method of claim 24, wherein administering light in multiple discrete applications includes administering an amount of radiation of about 5 mj/cm$^2$ to 100 j/cm$^2$ during each of the discrete applications.

27. The method of claim 22, wherein administering light to the infection includes administering light with a xenon light source.

28. The method of claim 22, wherein administering light to the infection includes administering a multispectrum light having a substantial portion of the administered light of about 100 nm to 400 nm.

29. The method of claim 22, wherein administering light to the infection includes administering a multispectrum light having a substantial portion of administered light of about 170 nm to 2600 nm.

30. The method of claim 22, wherein administering light to the infection includes administering a pulsed polychromatic light having a substantial portion of the administered light of about 100 nm to 400 nm.

31. The method of claim 22, wherein administering light to the infection includes administering a broad spectrum pulse light source.

32. The method of claim 22, wherein administering light to the infection includes administering light of about 240 nm to 280 nm.

33. The method of claim 22, wherein administering light to the infection includes administering light of about 240 nm to 315 nm.

34. The method of claim 22, wherein administering light to the infection includes administering light outside of the ultraviolet range to enhance treatment of the infection.

35. The method of claim 22, wherein the infection is in a nail of the patient.

36. The method of claim 22, wherein the patient is an animal.

37. The method of claim 22, further comprising, administering light to area with the infection prior to detecting visible signs of the infection.

38. A method of treating a microbial infection in a nail of a patient comprising:
   administering electromagnetic radiation of about 100 to 280 nm to an infected nail of the patient for a time and at a proximity and intensity sufficient to render microbes in the infection substantially incapable of reproducing by disruption of cellular processes of the microbes while insufficient to kill all of the microbes.

39. The method of claim 38, wherein administering electromagnetic radiation causes dimerization of at least some pyrimidine molecules of at least one of the RNA or DNA of the microbes.

40. The method of claim 38, wherein administering electromagnetic radiation to the infection does not cause severe erythema of area surrounding the infection.

41. The method of claim 38, wherein administering electromagnetic radiation to the infection does not excessively heat area with the infection or area surrounding the infection.

42. The method of claim 38, where administering electromagnetic radiation to the infection includes administering electromagnetic radiation to multiple locations in a single application.

43. The method of claim 38, wherein administering electromagnetic radiation to the infection includes administering electromagnetic radiation in multiple discrete applications.

44. The method of claim 43, wherein administering electromagnetic radiation in discrete applications includes administering an amount of radiation of about 5 to 10,000 $mj/cm^2$ to the infection during each of the discrete applications.

45. The method of claim 43, wherein administering light in multiple discrete applications includes administering an amount of radiation of about 5 $mj/cm^2$ to 100 $j/cm^2$ during each of the discrete applications.

46. The method of claim 38, wherein administering electromagnetic radiation to the infection includes administering light with a xenon light source.

47. The method of claim 38, wherein administering electromagnetic radiation to the infection includes administering a multispectrum light having a substantial portion of the administered light of about 240 nm to 280 nm.

48. The method of claim 38, wherein administering electromagnetic radiation to the infection includes administering a multispectrum light having a substantial portion of administered light of about 170 nm to 2600 nm.

49. The method of claim 38, wherein administering electromagnetic radiation to the infection includes administering a pulsed polychromatic light having a substantial portion of the administered light of about 240 nm to 280 nm.

50. The method of claim 38, wherein administering electromagnetic radiation to the infection includes administering a broad spectrum pulse light source and administering at least 1.25 $J/cm^2$ of energy to the infection.

51. The method of claim 38, further comprising:
   evaluating the infection;
   calculating an amount of energy required to inactivate the microbes in the infection; and
   calculating an amount of the light of about 240 nm to 280 nm that is required to be administered to achieve the required amount of energy, wherein calculating includes taking into account at least depth of area with the infection through which the light must be transmitted.

52. The method of claim 38, wherein administering electromagnetic radiation to the infection includes administering light outside of the ultraviolet range to enhance treatment of the infection.

53. The method of claim 38, wherein the patient is an animal.

54. The method of claim 38, further comprising, administering electromagnetic radiation to area with the infection prior to detecting visible signs of the infection.

* * * * *